(12) United States Patent
Fey et al.

(10) Patent No.: US 6,640,000 B1
(45) Date of Patent: Oct. 28, 2003

(54) METHOD AND APPARATUS FOR ANALYZING IMAGES

(76) Inventors: Stephen J. Fey, Vestervang 772, DK-8000 Aarhus C (DK); Peter Mose Larsen, Valmuemarken 16, DK-5260 Odense S (DK)

(*) Notice: Subject to any disclaimer, the term of this patent is extended or adjusted under 35 U.S.C. 154(b) by 0 days.

(21) Appl. No.: 09/254,675
(22) PCT Filed: Sep. 16, 1997
(86) PCT No.: PCT/IB97/01114
§ 371 (c)(1),
(2), (4) Date: Jun. 21, 1999
(87) PCT Pub. No.: WO98/11508
PCT Pub. Date: Mar. 19, 1999

Related U.S. Application Data
(60) Provisional application No. 60/031,291, filed on Sep. 16, 1996, and provisional application No. 60/029,325, filed on Oct. 25, 1996.

(51) Int. Cl.[7] ............................................... G06K 9/00
(52) U.S. Cl. .................................... 382/128; 435/6
(58) Field of Search ............................... 382/128, 129, 382/199, 130, 131, 132, 133; 356/42, 39, 318, 320; 435/6, 7.2, 7.23; 436/10, 63, 64, 8

(56) References Cited

U.S. PATENT DOCUMENTS

| | | | |
|---|---|---|---|
| 4,618,937 A | * 10/1986 | Elias et al. | 364/518 |
| 4,885,697 A | * 12/1989 | Hubner | 702/27 |
| 5,400,249 A | 3/1995 | Soll et al. | |
| 5,073,963 A | 7/1996 | Samons et al. | 382/30 |
| 5,541,064 A | * 7/1996 | Bacus | 435/6 |
| 5,666,434 A | * 9/1997 | Nishikawa et al. | 382/128 |
| 5,872,860 A | * 2/1999 | Shen et al. | 382/128 |

OTHER PUBLICATIONS

Andersen, H.U., et al., "Genetically determined differences in newborn rat islet sensitivity to interleukin-1 in vitro: no association with the diabetes prone phenotype in the BB-rat," *Acta Endocrinologica (Copenh)* 120:92–98, Copenhagen, Munksgaard (1989).

Andersen, H.U., et al., "Nicotinamide Prevents Interleukin-1 Effects on Accumulated Insulin Release and Nitric Oxide Production in Rat Islets of Langerhans," *Diabetes* 43:770–777, American Diabetes Association (1994).

Andersen, H.U., et al., "Two–Dimensional Gel Electrophoresis of Rat Islet Proteins. Interleukin 1β–Induced Changes in Protein Expression Are Reduced by L–Arginine Depletion and Nicotinamide," *Diabetes* 44:400–407, American Diabetes Association (Apr. 1995).

Appel, R.D., et al., "The MELANIE project: From a biopsy to automatic protein map interpretation by computer," *Electrophoresis* 12:722–735, VCH Verlagsgesellschaft mbH (1991).

Christensen, U.B., et al., "Islet Protein Expression at Diabetes Onset in BB–Rats Differs from that Seen During Islet Allograft Rejection," *Diabetologia* 38(*Suppl 1*):A85, Abstract No. 327, Springer–Verlag (Aug. 1995).

Eizirik, D.L., et al., "The harmony of the spheres: inducible nitric oxide synthase and related genes in pancreatic beta cells," *Diabetologia* 39:875–890, Springer–Verlag (Aug. 1996).

(List continued on next page.)

Primary Examiner—Jayanti K. Patel
Assistant Examiner—Seyed Azarian
(74) Attorney, Agent, or Firm—Sterne, Kessler, Goldstein & Fox P.L.L.C.

(57) ABSTRACT

A method and apparatus for analyzing images is provided that uses a master composite image, generated by averaging selected images, to analyze and interpret an existing or new image. This significantly reduces the amount of time and operator effort required to interpret an image. The invention also provides for comparison between individual images. The present invention can be used for analyzing gel electrophoresis images to identify new proteins, and to compare gel images to identify changes in proteins.

14 Claims, 14 Drawing Sheets

OTHER PUBLICATIONS

Eizirik, D.S., et al., "Role of Receptor Binding and Gene Transcription for Both the Stimulatory and Inhibitory Effects of Interleukin–1 in Pancreatic β–Cells," *Autoimmunity* 12:127–133, Harwood Academic Publishers GmbH (1992).

Garrels, J.I., et al., "The QUEST System for Quantitative Analysis of Two–dimensional Gels," *J. Biol. Chem.* 264:5269–5282, American Society of Biochemistry and Molecular Biology, Inc (1989).

Giometti, C.S., et al., "Mouse liver protein database: A catalog of proteins detected by two–dimensional gel electrophoresis," *Electrophoresis* 13:970–991, VCH Verlagsgesellschaft mbH (1992).

Grunberger, G., et al., "Insulin Receptors in Normal and Disease States," *Clin. Endocrinol. Metab.* 12:191–219, W.B. Saunders Company Ltd. (1983).

Helqvist, S. et al., Interleukin 1 induces new protein formation in isolated rat islets of Langerhans, *Acta Endocrinologica (Copenh)* 121:136–140, Copenhagen, Munksgaard (1989).

Helqvist, S., et al., "Heat shock protein induction in rat pancreatic islets by recombinant human interleukin 1β," *Diabetologia* 34:150–156, Springer–Verlag (1991).

Hughes, J.H., et al., "Interleukin 1 Inhibits Insulin Secretion from Isolated Rat Pancreatic Islets by a Process That Requires Gene Transcription and mRNA Translation," *J. Clin. Invest.* 86:856–863, American Society for Clinical Investigation (1990).

Jin, J.S., et al., "Shape Representations and Pattern Matching Under the Multi–Channel Theory," *Proceedings of the 3rd Pacific Rim International Conference on Artificial Intelligence*, International Academic Publishers, Beijing, China, Aug. 15–18, vol. 2, pp. 970–975 (1994).

Jungblut, P., et al., "Protein analysis on a genomic scale," *J. Biotech.* 41:111–120, Elsevier Science B.V. (Jul. 1995).

Jungblut, P., et al., "Quantitative Analysis of Two–Dimensional Electrophoretic Protein Patterns: Comparison of Visual Evaluation with Computer–Assisted Evaluation," in *Electrophoresis '84*, Neuhoff, V., ed., Verlag ChemieGmbH, Göttingen, pp. 310–303, (1984).

Karlsen, A.E., et al., "Cloning and Expression of Cytokine–Inducible Nitric Oxide Synthase cDNA from Rat Islets of Langerhans," *Diabetes* 44:753–758, American Diabetes Association (Jul. 1995).

Karlsen, A.E., et al., "Identification and Characterization of Proteins Involved in Cytokine Mediated β–Cell Destruction and Insulin–Dependent Diabetes Mellitus," *Cytokine* 9:912, Abstract No. 90, Academic Press (Nov. 1997).

Knecht, M., et al., "Dilated Cardiomyopathy: Computer–Assisted Analysis of Endomyocardial Biopsy Protein Patterns by Two–Dimensional Gel Electrophoresis," *Eur. J. Clin. Chem. Clin. Biochem* 32:615–624, Walter de Gruyter & Co. (1994).

Korsgren, O., et al., "Hyperglycemia–induced B Cell Toxicity. The Fate of Pancreatic Islets Transplanted into Diabetic Mice Is Dependent on Their Genetic Background," *J. Clin. Invest.* 86:2161–2168, American Society for Clinical Investigation, Inc. (1990).

Manabe, T., et al., "Studies on the procedure for the construction of cellular protein databases employing micro Two–Dimensional electrophoresis: An HL–60 protein database," *Electrophoresis* 16:407–422, VCH Verlagsgesellschaft mbH (Mar. 1995).

Mandrup–Poulsen, T., "The role of interleukin–1 in the pathogenesis of IDDM," *Diabetologia* 39:1005–1029, Springer–Verlag (Sep. 1996).

Mandrup–Poulsen, T., "Islet Cytotoxicity of Interleukin 1: Influence of Culture Conditions and Islet Donor Characteristics," *Diabetes* 36:641–647, American Diabetes Association (1987).

Martin, J.–P., "Intelligent imaging automates gel analysis for molecular biology," *Scientific Computing World*, pp. 25–28, Cambridge Publishers Ltd. (Sep. 1995).

Microsoft Corporation, Microsoft Excel User's Guide, Microsoft Corporation, pp. 305–316 (1992–1993).

O'Farrell, P. H., "High Resolution Two–Dimensional Electrophoresis of Proteins," *J. Biol. Chem.* 250:4007–4021, American Society of Biological Chemists, Inc. (1975).

O'Farrell, P.Z., et al., "High Resolution Two–Dimensional Electrophoresis of Basic as Well as Acidic Proteins," *Cell* 12:1133–1141, MIT Press (1977).

Pociot, F., et al., "A Comprehensive Approach to Identifying New Susceptibility Genes to Insulin–Dependent Diabetes Mellitus—Combining Proteome and Genome Anayses," *Cytokine* 9:899, Abstract No. 39, Academic Press (Nov. 1997).

Shi, C.Z., et al., "Protein Databases for Compacted Eight–Cell and Blastocyst–Stage Mouse Embryos," *Mol. Reprod. Develop.* 37:34–47, Wiley–Liss, Inc. (1994).

Steiner, S., et al., "Protein variability in male and female Wistar rat liver proteins," *Electrophoresis* 16:1969–1976, VCH Verlagsgesellschaft mbH (Oct. 1995).

von Herrath, M.G., et al., "Oral Insulin Treatment Suppresses Virus–induced Antigen–specific Destruction of β Cells and Prevents Autoimmune Diabetes in Transgenic Mice," *J. Clin. Invest.* 98:1324–1331, The American Society for Clinical Investigation, Inc. (Sep. 1996).

Wadhwa, R., et al., "Identification of a Novel Member of Mouse hsp70 Family," *J. Biol. Chem.* 268:6615–6621, American Society for Biochemistry and Molecular Biology (1993).

Wadhwa, R., et al., "Induction of Cellular Senescence by Transfection of Cytosolic Mortalin cDNA in NIH 3T3 Cells," *J. Biol. Chem.* 268:22239–22242, American Society for Biochemistry and Molecular Biology (1993).

Welsh, N., et al., "Interleukin–1β Increases the Biosynthesis of the Heat Shock Protein hsp70 and Selectively Decreases the Biosynthesis of Five Proteins in Rat Pancreatic Islets," *Autoimmunity* 9:33–40, Harwood Academic Publishers GmbH (1991).

Wilkins, M.R., et al., "From Proteins to Proteomes: Large Scale Protein Identification by Two–Dimensional Electrophoresis and Amino Acid Analysis," *Bio/technology* 14:61–65, Nature Publishing Co. (Jan. 1996).

Wilm, M., et al., "Femtomole sequencing of proteins from polyacrylamide gels by nano–electrospray mass spectrometry," *Nature* 379:466–469, Nature Publishing Co. (Feb. 1996).

Young, D. S. and Tracy, R. P., "Clinical applications of two–dimensional electrophoresis," *Chromatography A* 698:163–179, Elsevier Science B.V. (Apr. 1995).

Co–Pending Non–Provisional U.S. patent application No. 09/297,034, Nerup, J., et al., filed Apr. 26, 1999, 102(e) date Jul. 21, 1999.

Co–Pending Non–Provisional U.S. patent application No. 09/297,040, Larsen, P.M., et al., filed Apr. 26, 1999, 102(e) date Jul. 21, 1999.

\* cited by examiner

METHOD AND APPARATUS FOR ANALYZING IMAGES

This application is a 371 of PCT/IB97/01114 filed Sep. 16, 1997 and claims benifit of Prov. No. 60/031,291 filed Sep. 16, 1996 and No. 60/029,325 filed Oct. 25, 1996.

BACKGROUND OF THE INVENTION

1. Field of the Invention

The invention relates to method and apparatus for analyzing images, and more particularly to comparing related or similar images (black and white or color). The invention relates in preferred embodiments to a computer-based process, a computer-based system, a computer program, and/or a computer program product for analyzing gel electrophoresis images to identify new proteins or proteomes, and/or to compare gel images to identify quantitative or qualitative changes in proteins.

2. Related Art

Because of acidic and/or basic side chains, proteins include positively and/or negatively charged groups. The behavior of a protein in an electric field is determined by the relative numbers of these positive and/or negative charges, which in turn are affected by the acidity of the solution. At the isoelectric point (pI), the positive and negative charges are exactly balanced and the protein shows no net migration. Proteins with a pI less than about 7.5 are usually analyzed in isolelectric focusing (IFE) gels. The pH gradient in these gels is usually preformed and the sample applied at the neutral end of the gel (all acidic proteins—proteins with a pI smaller than 7.5—will be charged negatively). At the start of electrophoresis, all the negatively charged proteins will start to migrate towards the anode, i.e. through the gel. As each protein reaches its pI, the electrical forces on the protein from the cathodic and anodic sides become equal and the protein thus "focuses." Proteins with a pI greater than 7 are best resolved on non-equilibrium pH gradient electrophoresis (NEPHGE) gels. Hence the proteins are applied again at the neutral pH region and all basic proteins (with a pI greater than 7) will be charged positively. During electrophoresis, they will therefore move towards the cathode, i.e., through the gel.

Obviously, the same separation could be obtained in an immobilized pH gradient electrophoresis gel system (IPG) where the pH gradient is covalently bound to the support matrix (polyacrylamide). Different proteins have different proportions of acidic and/or basic side chains, and hence have different isoelectric points. In a solution of a particular hydrogen ion concentration (pH), some proteins move toward a cathode and others toward an anode. Depending upon the size of the charge as well as upon molecular size and/or shape, different proteins move at different speeds. This difference in behavior in an electric field is the basis of the electrophoresis method of separation and/or analysis of proteins.

Two-dimensional gel electrophoresis (2DGE) is a particularly effective tool for analyzing proteins. Cell extracts from any prokaryotic or eukaryotic cell are put onto a gel, and the individual proteins are separated first by the pI (first dimension) and then by size (second dimension). The result is a characteristic picture of as many as 1000 to 5000 spots, each usually a single protein. Resolution is improved by increasing gel composition or size, and/or by enhancing the sensitivity through the use of radiochemical methods, silver staining, and/or the reduction in thickness of the gels to 1.5 mm or less. Jungblut et al. have reported up to 5000 protein spots of mouse brain on gels of size 23×30 cm (*Journal of Biotechnology*, 41 (1995) 111–120).

High resolution 2DGE has been used for analyzing basic as well as acidic proteins. Isoelectric focusing (IEF) in the first dimension can be combined with sodium dodecyl sulfate (SDS) gel electrophoresis in the second dimension (IEF-SDS). Alternatively, nonequilibrium pH gradient electrophoresis (NEPHGE) in the first dimension can be combined with SDS gel electrophoresis in the second dimension (NEPHGE-SDS). Such procedures are known in the art, e.g., as described in O'Farrell, *J. Biol. Chem.* 250, 4007–4021 (1975) and O'Farrell et al., *Cell*, 12:1133–1142 (1977), the entirety of which are incorporated herein by reference. Gels cannot be used for the determination of absolute isoelectric points, but rather to an observed value due to the fact that the running conditions, e.g., high urea concentration, are not ideal (in the physical-chemistry meaning of the word—the pKa values of the side chains are rather different between water and high concentrations of urea). NEPHGE gels cannot be used for the determination of absolute isoelectric points of proteins. The isoelectric point of a protein is usually determined in reference to a stable pH gradient formed during isoelectric focusing. As discussed in O'Farrell (1977), the best resolution of acidic proteins is obtained with equilibrium IEF since the region of the gels containing acidic proteins is compressed in NEPHGE. The best resolution of basic proteins is with a pH 7–10 NEPHGE gel. For the highest resolution of the entire range of proteins, two gels are preferably used: (1) an IEF gel for acidic proteins; and (2) a NEPHGE gel for basic proteins. Of course, the precise image obtained depends upon many factors including, but not limited to, chemicals such as ampholytes, physical parameters such as gel dimensions and/or temperature and/or the electrical parameters employed.

Once a 2DGE gel is run, the image can be revealed by a number of ways including: staining (e.g., with Coomassie blue, silver or fluorescent or immunological staining); direct measurement of the radioactivity (using devices that can detect the radioactivity (including so-called β-imagers, or phosphor image technologies); or photographic film sensitive to the radioactivity); fluorescent enhancement of the radiographic emissions (using various fluorophores) or combinations of the above. In addition, samples can be treated before electrophoresis (e.g., with monobromobimane and related compounds) so that the proteins are detectable after electrophoresis using some of the above methods. For example, after electrophoresis, a 2DGE gel can be fixed with methanol and acetic acid, treated with AMPLIFY® (Amersham), and dried. The gel is then placed in contact with X-ray film and exposed. The gel can be exposed for multiple time periods to compensate for the lack of dynamic range of X-ray films. Each film image comprises a multiplicity of "spots" of differing position, size, shape, and/or optical density. The spots on the image are analyzed to determine the correspondence between spots and proteins.

Manual visual inspection and analysis of gel images can be done under controlled conditions and within specific ranges (Jungblut et al., Quantitative analysis of two-dimensional electrophoretic protein patterns: Comparison of visual evaluation with computer-assisted evaluation. In: Neuhoff, V. (Ed.) Electrophoresis '84, Verlag Chemie GmbH, Weinheim, 301–303 and Andersen et al., *Diabetes*, Vol. 44, April 1995, 400–407). Analysis of one film can take in excess of eight hours, even for one having significant skill and experience in this art. Typically, certain methods of obtaining images of the gels are non-linear (e.g., silver staining and/or X-ray film) and it is often necessary to make corrections for this if the full range of protein expression is to be covered (this can be up to a ratio of 1:100,000 for the protein of lowest to highest expression). Further, quantification with visual analysis is limited. Typically, visual analysis only detects changes in protein amounts of a factor greater than or equal to 2.

Various computer programs and computer evaluation systems have been developed to improve quantification and assist in evaluation of gel films, e.g., PDQUEST (Protein Database Inc., New York), BioImage (Millipore, Bedford, Mass.), Phoretix (Phoretix International, Newcastle, UK), and Kepler (Large Scale Biology Corporation, Rockville, Md.). To use a computer program such as BioImage (BioImage, Ann Arbor, Mich.), the image of the gel on the film is scanned into a computer. The digitized gel image is analyzed by the computer program. Each spot is assigned an intensity value, such as an integrated optical density percentage (IOD %), and a position on the gel, such as an "X,Y" Cartesian-type coordinate. Computer programs such as BioImage require the highest qualities in resolution and reproducibility of the spot position. Because the gel medium is so elastic, gel patterns are not identical, i.e., two gels, run under essentially identical conditions, will not have each protein spot located in exactly the same position. If two gels are run under conditions that are not essentially the same, then the variations in position of corresponding protein spots will be even greater.

Computer evaluation systems such as those described above have improved the quantification of spot intensities and IOD % for generation of a "spot list" for a gel image. However, computer evaluation systems such as those described above still require significant operator effort for editing. A gel image to be evaluated is input to a computer, such as by scanning. The digitized image is searched to locate spots having an intensity or optical density above a sensitivity threshold. The operator must then edit the gel image. For example, if two very big spots are close together, the computer may have identified the two spots as one elongated spot. The computer may not be able to resolve that there are actually two spots. The operator would then be required to manually edit the image to divide the spot into two spots. As another example, the computer may incorrectly identify as a protein spot a non-protein spot on the gel image, such as a high intensity streak. The operator would then be required to manually edit the image to delete the non-protein spot. It can take from six to eight hours for a skilled operator to edit a gel image evaluated using a conventional computer evaluation system.

As reported in *Jungblut* et al. (1995), numerous researchers have used conventional computer evaluation systems to produce 2DGE databases for various tissues or cell types. However, these systems require significant effort on the part of the operator to produce an accurate spot list for a new gel image. More importantly, conventional computer evaluation systems do not provide an analysis and/or interpretation tool that uses information from other gel images of the same cell type to allow an operator to quickly and/or efficiently analyze and/or interpret a new gel image. Conventional computer evaluation systems cannot be used to reliably detect proteins only present in small amounts. Thus, there is a need in the art for a computer-based analysis system that reduces the effort required by the operator, and increases the speed with which new gel images can be analyzed and/or interpreted. There is a further need in the art for a computer-based analysis system for analyzing and/or interpreting new gel images that uses information from other gel images of the same cell type.

Conventional computer evaluation systems also do not provide the full analysis tools for statistical comparison between groups of gel images. Thus, there is a further need in the art for a computer-based analysis system that is capable not only of analyzing and/or interpreting a new gel image, but also of executing statistical comparisons between various groups of gel images.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention is directed to methods, compounds, compositions and apparatus for analyzing images of electrophoresis gels. These images can be in black and white or in color (a colored image can have three grey scale ranges for the primary colors and can thus be analyzed in the same way as described below). For the purposes of this description only, one grey scale is considered although for one skilled in the art, there would be no difficulty to extend the description to the three primary colors, or combinations thereof.

Any type of image could be analyzed in the a manner described below—although the method would be best suited for the analysis or comparison of any type of situation where two or more similar images are obtained, for example sequential satellite photographs of clouds or land surfaces to chart weather patterns or in geological surveying. Other examples would include serial sections of biopsies, serial scanning runs from CT or CAT devices in hospitals. In biotechnology, applications can include, but not be limited to, Northern, Southern or Western blots, 1-D gels and/or 2DGE gels. The present invention is described below with respect to analyzing gel electrophoresis images to identify proteins, and to compare gel images to identify changes in proteins or nucleic acids.

In one aspect of the invention, a method for analyzing images is provided. The method comprises one or more of the following steps, such as, but not limited to (1) at least one of (3), (4), (5), (6), (7), (8), (9), (10), (11) or (12):

(1) capturing a new image, wherein the new image contains a plurality of new image spots, each new image spot having a spot number, an integrated optical density percentage (IOD %) and a position;

(2) generating a master composite image for use in analyzing the new image, wherein the master composite image contains a plurality of master composite spots, each master composite spot having a spot number, an IOD % and a position;

(3) generating a master composite, wherein the master composite comprises the spot number, the IOD %, the position, the variability of the spot (for example the standard deviation expressed as a percentage) for the position and IOD %, and a saturation value (corresponding to the value of the maximum pixel intensity found in any of the spots (from the original images which were used to derive the spot in question) (this value is expressed as a fraction on a scale from white (0) to black (1)) for each of the plurality of master composite spots;

(4) aligning the new image with the master composite image;

(5) selecting a set of anchor points from the master composite;

(6) detecting new image spots that have a position that is within a position tolerance of the position of corresponding anchor points and that have an IOD % that is within an IOD % tolerance of the IOD % of corresponding anchor points, and matching the detected new image spots to the corresponding anchor points to form a set of matched new image spots;

(7) calculating a set of vectors linking spots of the same number in the master composite image and in the new gel image; and determining for each vector the length and angle;

(8) calculating a vector difference for each of the set of matched new image spots corresponding to the difference between the vector in question and the vectors originating from a number (for example about 2–500) of the nearest spots to the spot in question. This will generate a vector difference for each of the new matched new image spots and in a subsequent step, removing from the set of matched new image spots those matches for which the vector differences are greater than a predetermined percentage of the best (shortest length and numerically smaller angle) vector differences. A manner by which these vector differences can be used to quality check the alignment of the images and to guide the correction of mismatches in a reiterative manner until an optimal match is obtained;

(9) selecting a set of well-defined spots from the master composite, detecting new image spots that have a position that is within a position tolerance of the position of corresponding well-defined spots, matching the detected new image spots to the corresponding well-defined spots, and adding the matched new image spots to the set of matched new image spots;

(10) selecting a set of saturated spots from the master composite, detecting new image spots that have a position that is within a position tolerance of the position of corresponding saturated spots, matching the detected new image spots to the corresponding saturated spots, and adding the matched new image spots to the set of matched new image spots;

(11) selecting a set of weak spots from the master composite, detecting new image spots that have a position that is within a position tolerance of the position of corresponding weak spots, matching the detected new image spots to the corresponding weak spots, and adding the matched new image spots to the set of matched new image spots; and

(12) searching the new image outside the set of matched new image spots to locate unidentified new image spots.

In another aspect of the present invention, the method further includes comparing a first set of images to a second set of images.

In yet a further aspect of the present invention, the new image is aligned with the master composite image through the use of a common anchor point. Common anchor points correspond to spots present in both the new image and the master composite image. Anchor points selected from the master composite can include primary anchor points and secondary anchor points. Primary and secondary anchor points are obtained at different stages in the image processing using different selection criteria to select the master composite proteins to be used.

In still a further aspect of the present invention, well-defined spots have a saturation value S in the range of about $0.2 < S < 0.8$. Saturated spots have a saturation value $S \geq 0.8$. Weak spots have a saturation value $S \leq$ about 0.2.

In still a further aspect of the present invention, a computer program product is provided that has computer program logic recorded thereon for enabling a processor in a computer system to analyze two-dimensional electrophoresis gel images of cell proteins. Such computer program logic includes the one or more of the following:

at least one algorithm, sub-routine, routine or image capturing means for enabling the processor to receive data representing a new gel image, wherein the new gel image contains a plurality of new gel image spots that correspond to proteins on the new gel image, each new gel image spot having an integrated optical density percentage (IOD %) and a position;

at least one algorithm, sub-routine, routine or master composite image generating means for enabling the processor to generate a master composite image for use in analyzing the new gel image, wherein the master composite image contains a plurality of master composite spots that correspond to proteins on the master composite image, each master composite spot having a spot number, an IOD % and a position;

at least one algorithm, sub-routine, routine or master composite generating means for enabling the processor to generate a master composite, wherein the master composite comprises a spot number, the position, the IOD %, and a saturation value (corresponding to the value of the maximum pixel intensity found in any of the spots (from the original images which were used to derive the spot in question) (this value is expressed as a fraction on a scale of from white (0) to black (1)) for each of the plurality of master composite spots;

at least one algorithm, sub-routine, routine or aligning means for enabling the processor to align the new gel image with the master composite image;

at least one algorithm, sub-routine, routine or selecting means for enabling the processor to select a set of anchor points from the master composite;

at least one algorithm, sub-routine, routine or anchor point detecting and matching means for enabling the processor to detect new gel image spots that have an IOD % that is within an IOD % tolerance of the IOD % of corresponding anchor points, and match the detected new gel image spots to the corresponding anchor points to form a set of matched new gel image spots;

at least one algorithm, sub-routine, routine or means for enabling the processor to calculate a set of vectors linking spots of the same number in the master composite image and in the new gel image; and determining for each vector the length and angle;

at least one algorithm, sub-routine, routine or vector differencing means for enabling the processor to calculate a vector difference for each of the set of matched new image spots corresponding to the difference between the vector in question and the vectors originating from a number (for example about 1–500) of the nearest spots to the spot in question. (This will generate a vector difference for each of the new matched new image spots and in a subsequent step, removing from the set of matched new images spots those matches for which the vector differences are greater than a predetermined percentage of the best (shortest length and/or numerically smallest angle) vector differences. For highly saturated spots (less than about >3–40 saturated pixels, less than about >9 pixels), the position of the spot center is determined using. e.g., the spot shape characteristics. Allowances can be made for cases where the saturation areas covers more than one spot and the saturation area is divided up into a number of areas corresponding to the number of spots existing in the MCI and spot centers can be calculated based on these allowances, as further known in the art or as described herein);

at least one algorithm, sub-routine, routine or means by which these vector differences can be used to quality check the alignment of the images and to guide the correction of mis-matches in a reiterative manner until an optimal match is obtained;

at least one algorithm, sub-routine, routine or means for enabling the processor to calculate how these vector differences can be used to quality check the alignment and to guide the correction of mismatches in a reiterative manner until an optimal match is obtained;

at least one algorithm, sub-routine, routine or well-defined spot detecting and matching means for enabling the processor to select a set of well-defined spots from the master composite, to detect new gel image spots that have a position that is within a position tolerance of the position of corresponding well-defined spots, to match the detected new gel image spots to the corresponding well-defined spots, and to add the matched new gel image spots to the set of matched new gel image spots;

at least one algorithm, sub-routine, routine or saturated spot detecting and matching means for enabling the processor to select a set of saturated spots from the master composite, to detect new gel image spots that have a position that is within a position tolerance of the position of corresponding saturated spots, to match the detected new gel image spots to the corresponding saturated spots, and to add the matched new gel image spots to the set of matched new gel image spots;

at least one algorithm, sub-routine, routine or weak spot detecting and matching means for enabling the processor to select a set of weak spots from the master composite, to detect new gel image spots that have a position that is within a position tolerance of the position of corresponding weak spots, to match the detected new gel image spots to the corresponding weak spots, and to add the matched new gel image spots to the set of matched new image spots;

at least one algorithm, sub-routine, routine or unidentified spot locating means for enabling the processor to search the new gel image outside the set of matched new gel image spots to locate unidentified new gel image spots; and at least one algorithm, sub-routine, routine or comparing means for enabling the processor to compare a first set of gel images to a second set of gel images.

In still a further aspect of the present invention, the comparing means includes the following:

at least one algorithm, sub-routine, routine or first set analyzing means for enabling the processor to compute a statistical average of IOD % for each spot in the first set;

at least one algorithm, sub-routine, routine or second set analyzing means for enabling the processor to compute a statistical average of IOD % for each spot in the second set; and at least one algorithm, sub-routine, routine or statistical average differencing means for enabling the processor to determine if each spot in the first set is statistically different from each spot in the second set.

In still a further aspect of the present invention, the comparing means provides the possibility to combine different exposures of the same gel or different gels of the same sample in different amounts in such a way that the effective dynamic range of the protein detection system (selected from the list given above) can be increased.

Features and Advantages

It is a feature of the present invention that it can analyze and/or interpret new gel images, and/or also conduct statistical comparisons between groups of gel images.

It is a further feature of the present invention that it uses information from a single gel (using default tolerance values) or a master composite image to guide the analysis and interpretation of new or additional gel images.

It is yet a further feature of the present invention that it uses the integrated optical density percentage, as well as the position, in locating spots in new gel images.

It is an advantage of the present invention that new gel images can be analyzed and/or interpreted with minimal input from an operator.

It is a further advantage of the present invention that new gel images can be analyzed and/or interpreted quickly and/or efficiently.

It is a still further advantage of the present invention that it can reliably detect proteins that are present in small amounts.

It is yet a further advantage of the present invention that it is not limited to analysis and/or interpretation of two-dimensional gel electrophoresis images, and can be used to compare any two similar images, whether black and white or color or in any situation where image interpretation and/or recognition is involved. This process could include the comparison of "freshly derived images" from any image capture device with an image recovered from a computer memory device. In another embodiment, this could include the comparison of two sequential images (e.g., a video recording or real time video image) in order to identify the differences between the two.

BRIEF DESCRIPTION OF THE DRAWINGS

The present invention is described with reference to the accompanying drawings. In the drawings, like reference numbers indicate identical or functionally similar elements.

DETAILED DESCRIPTION OF THE EMBODIMENTS

1. Overview

Figure 1:
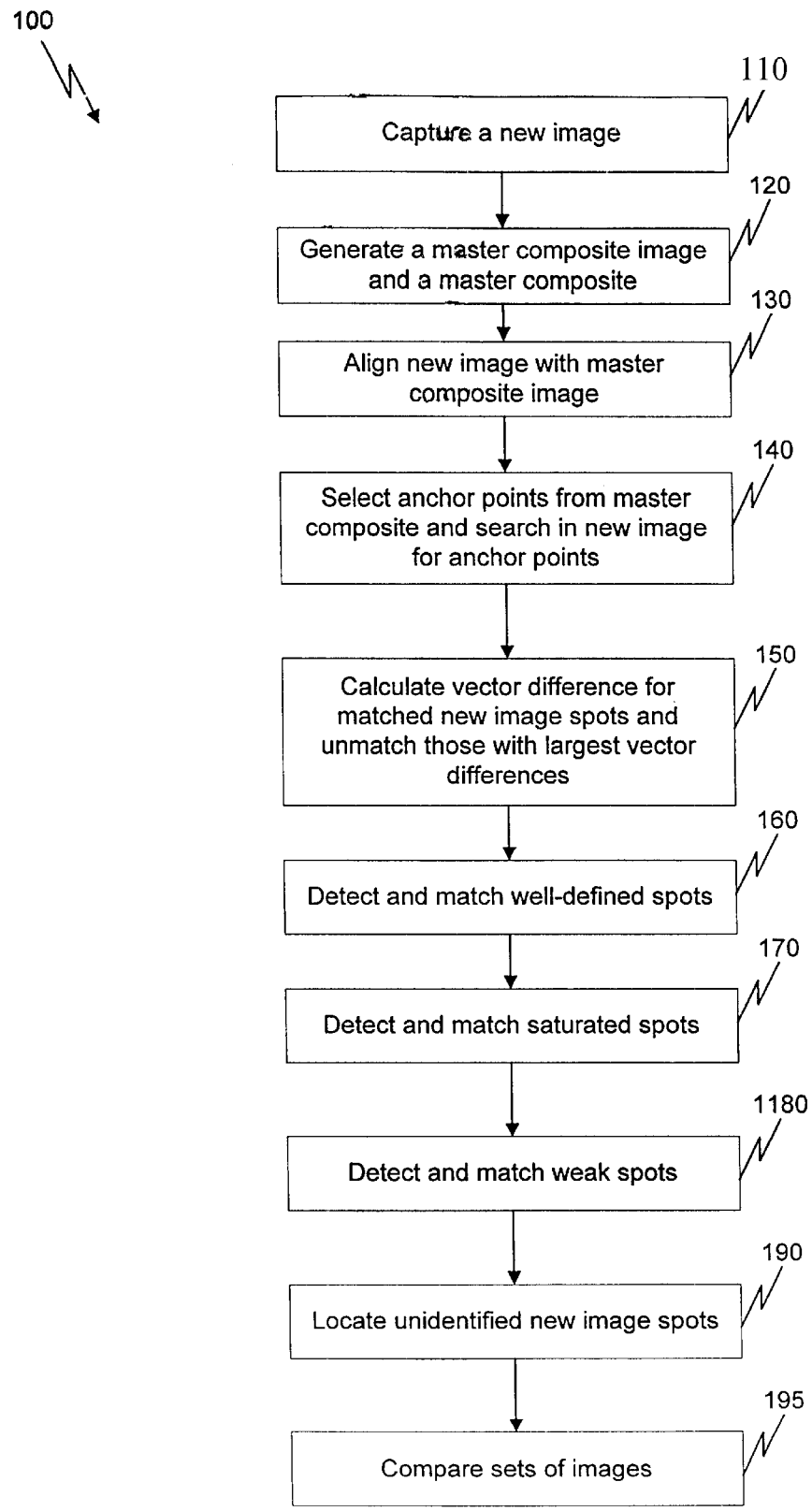
FIG. 1 shows a block diagram illustrating one embodiment of a method of the present invention.

The present invention is directed toward a computer-based process, a computer-based system and/or a computer program product for analyzing images. The present invention will be described in the context of analyzing two-dimensional gel electrophoresis (2DGE) images of proteins. However, it is to be understood that the present invention is not limited to analysis of 2DGE images, and can be used to compare any two similar images, whether black and white or color or in any situation where image interpretation and/or recognition is involved. This process could include the comparison of "freshly derived images" from any image capture device with an image recovered from a computer memory device. Examples of such images could include but are not restricted to: tissue sections, gel or blot images of proteins, RNA or DNA, section images from scanning devices like those used for computerized tomography (e.g., computer assisted tomography (CAT), positron emission tompgraphy (PET)), satellite images, star pictures, x-ray, fluorographs, or any recorded or real-time image.

The method of the present invention provides an analysis tool for analyzing and/or interpreting gel images quickly and/or efficiently with minimal operator input. The gel images are analyzed and/or interpreted so that new proteins can be identified. The method of the present invention also provides a comparison tool for comparing gel images to identify changes in proteins, i.e., up- or down regulation.

The method of the present invention uses information from a master composite image to guide the analysis of new gel images. In this manner, information from other gel images of the same cell type is used to guide the analysis and/or interpretation of a new gel image. This technique reduces significantly the time required to analyze a new gel image. This technique also reduces significantly the operator effort that is required to analyze a new gel image.

To carry out the method of the present invention, a master composite image is generated from images selected by an operator. The images selected by the operator for use in generating the master composite image would typically be of the same cell type, and would be relevant to the type of project or experiment being conducted. As used herein, "image" refers to a representation that is composed of pixels, each pixel having a grey level unit-less value assigned to it. For example, each pixel in an 8-bit image would have a grey level assigned to it ranging from zero (white) to 255 (black) and a saturation value (a value which varies from zero to 1, corresponding to the value of the darkest pixel of each spot divided by 255 (for 8 bit images)), and the standard deviation of the X,Y (positional) and Z (quantitation) values for each spot when the spot has been matched to more than one gel. An image with a higher number of bits would have a larger range of grey levels with finer steps.

A master composite is generated that corresponds to the master composite image. As explained in more detail below, the master composite includes data that represent characteristics of each spot on the master composite image, such as spot position, the integrated optical density percentage (IOD %), a spot number, and a saturation value. The master composite provides a compilation of data that can be readily searched to aid in the analysis analysis and/or interpretation interpretation of the new image. When a spot in the new image is located that corresponds to a spot in the master composite, the located new image spot is "matched" to the spot in the master composite. Once a master composite spot is matched to a new image spot, it is removed from the available pool of master composite spots. The method of the present invention iterates through a series of searches to match all of the master composite spots to new image spots. Any unmatched spots that are present in the new image after all of the master composite spots are matched represent unidentified new image spots. Such unidentified new image spots can represent previously unidentified proteins.

In another application of the present invention, different exposures of the same image of different gels of the same sample can be matched together so that it is possible to "extend the dynamic range" of the medium from which the image is read. This medium is typically, but not restricted to: X-ray film, silver or otherwise stained gels, immuno-stained gels or blots thereof, or combinations of these. This procedure can be useful in the present invention because: (i) the ratio of expression of proteins within a cell is greater than 100,000 (i.e., exceeding the dynamic range of response of X-ray film which is about 1,000 or stained gels which have a dynamic range of approximately 100); and/or (ii) because the response of the said medium is not linear (which introduces problems in accurate quantitation of the protein spots).

Once the master composite image is generated, the new image must be aligned to it. The method of the present invention aligns the new image to the master composite image through the use of anchor points. The anchor points include common anchor points that correspond to spots present in both the new image and the master composite image, and primary and secondary anchor points that are selected from the master composite based upon defined criteria. A vector differencing quality control analysis is carried out to ensure that the anchor points are properly matched to new image spots.

The method of the present invention carries out a search in the new image for three different types of spots present in the master composite that have not already been matched. The first type of spot is a "well-defined" spot. As explained more fully below, a well-defined spot is one having a saturation value "S" that is between about 0.2 and about 0.8. Well-defined spots are those spots that are not weak or saturated. The second type of spot is a "saturated" spot. A saturated spot has a saturation value S that is greater than or equal to about 0.8. The third type of spot is a "weak" spot. A weak spot has a saturation value that is less than or equal to about 0.2. Spots located in the new image that correspond to the well-defined, saturated, and weak spots are matched, and given the same spot number as the corresponding master composite spot. Once the search for the well-defined, saturated, and weak spots is complete, the new image outside of the matched new image spots is searched to locate unidentified spots. The unidentified spot search is carried out using two different sensitivity levels. The unidentified spots that are located are presented to the operator for further analysis and evaluation.

In another application of the present invention, different exposures of the same image can be matched together using the same procedures outlined above and described in detail below if the operator specifies that the new gel and the images selected as the MCI are either of the same gel or of the same sample. Following the combination of two or more images in these categories, the %IOD are recalculated and these values are used for further analysis.

The method of the present invention as described above provides an efficient analysis tool for analyzing and interpreting new images. The method of the present invention provides the additional capability of comparing various images that have previously been interpreted. For example, an operator can identify two or more groups of images to be compared, such as one group of cells treated in a particular manner, and one group of untreated cells. Each spot in the treated-cell group of gel images is compared to the corresponding spot in the untreated-cell group of gel images to see if there is a statistically significant difference. This provides a convenient way for an operator to do statistical comparison between selected images.

2. Method of the Present Invention

Turning now to FIG. 1, a block diagram 100 is shown that illustrates one embodiment of the method of the present invention. As explained more fully below, the invention may be implemented using hardware, software, or a combination thereof, and may be implemented in a computer system or other processing system. In a step 110, a new image is captured. It is to be understood that the present invention is not limited to a new image being a 2DGE gel image, so that the present invention can be used to analyze any suitable type of image. The image can be captured by scanning the image into a computer in a manner known to one of skill in the relevant arts. The image can also be captured by recovering it from a storage device, such as a random access memory (RAM), read only memory (ROM), hard disk drive, optical disk, floppy disk, etc. The image can also be captured by downloading it via a communications interface from another computer, camera, from a site via the INTERNET, or from any other source.

In a step 120, a master composite image and a master composite are generated and the type of analysis is selected (matching of new gel to master composite, two exposures of the same gel or two gels of the same sample). In a step 130, the new image is aligned with the master composite image.

In a step 140, anchor points are selected from the master composite. The new image is searched to locate in the new image spots that correspond to the anchor points. If a spot is located in the new image that corresponds to the anchor point, the new image spot is matched to the corresponding anchor point.

In a step 150, a vector difference is calculated for each matched new image spot. The matched new image spots that have the largest vector differences are unmatched.

In a step 160, the new image is searched to detect and match well-defined spots. In a step 170, the new image is searched to detect and match saturated spots. In a step 180, the new image is searched to detect and match weak spots.

In a step 190, the new image is searched to locate unidentified new image spots. The new image is searched outside of the spots that have already been matched.

If, at the beginning of the procedure (step 120) the operator has selected that the gels being matched were either two exposures of the same gel or two gels of the same sample, then the computer recalculations the %IOD for all proteins.

Finally, in a step 195, various sets of images can be compared. An operator can select groups of images to be compared, as well as the type of statistical comparison to be done.

Figure 2:
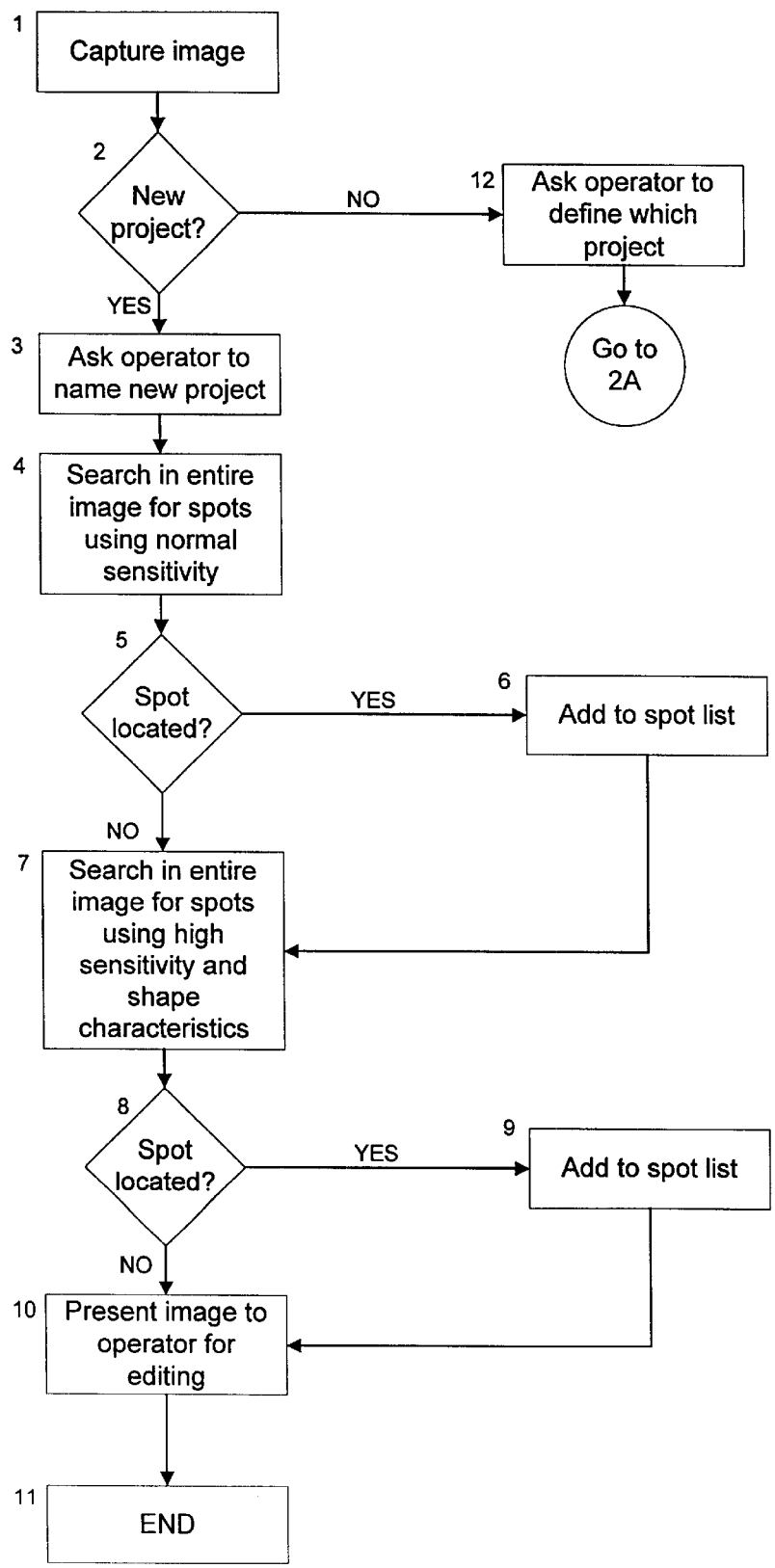
FIG. 2 shows a block diagram illustrating one embodiment for carrying out step 110 shown in FIG. 1.

Turning now to FIG. 2, a block diagram is shown that illustrates one embodiment for carrying out step 110. In step 1, the image is captured. An image is a computer picture in pixels and associated grey level values. The image corresponding to a gel is preferably stored in an individual image file. As explained more fully below, the image (pixels and grey level values) is processed to generate tables of image data that characterize the image. The image data is preferably stored in an image data file separate from the image (pixel) file.

In a decision step. 2, it is determined whether the image is associated with a new project. A project generally corresponds to an experiment. For example, a project can correspond to an experiment relating to a particular kind of cell, such as the islets of Langerhans (cells of the pancreas that secrete insulin), referred to herein as "islets". The experiment could include analysis and/or interpretation of one set of gels from normal islets, and another set of gels from islets treated in a particular way, such as with a cytokine or other biological molecules which interact with cells found in the islets. The experimental data for the project will include image files and corresponding image data files for both the normal islets and the treated islets. The experimental data for the project would preferably be stored together in a project "directory".

If the captured image does not correspond to a new project, then an image data file (and an image file) already exist for the captured image. In this case, the operator is asked to define which project is to be used in a step 12. Processing then continues at a step 13 by way of flow chart connector 2A (connectors 2A–9A are shown by circles in FIGS. 2–10, as discussed herein).

If the captured image does correspond to a new project, then processing continues in order to generate image data and an image data file for the captured image. In a step 3, the operator is asked to name the new project. In this manner, the image file for the captured image and the image data file for the captured image can be grouped together under a project name (such as in a computer directory having the project name). Processing then continues in a step 4.

In step 4, the entire captured image is searched for spots using normal sensitivity. To do so, the image file is searched looking for maxima that represent maxima in darkness or optical density. The maxima must be separated from each other by a predetermined distance (distance between spot centers). This is done to ensure that real maxima in optical density are located, not just local maxima generated by background noise. From each maxima, a number of radial vectors, e.g., 36, are sent out from the central maxima point. An integration is performed along each vector. A point of inflection is determined for each vector. The point of inflection on each vector represents a boundary point. The boundary points for all vectors are connected. The boundary generated by connecting the boundary points for all vectors represents the boundary of the detected spot in the captured image.

The area outside the boundary of the detected spot is analyzed to determine the average background around the spot. The average background is subtracted from all the pixels inside and including the boundary. This produces an integrated optical density (IOD) for the detected spot. The integrated optical density percentage (IOD %) is the IOD of a particular spot expressed as a percentage of the total IOD, computed by summing the IOD of all spots in the image.

It would be readily apparent to one of skill in the art how to carry out the search of step 4 as described above. There are a number of approaches to spot (or object) finding which would be readily apparent to one skilled in the art and the most appropriate algorithm should be selected for the task in hand. For example, a computer program such as BioImage can be used to carry out step 4.

In a decision step 5, it is determined whether a spot is located during the search in step 4. If a spot is located, then the spot is added to a spot list in a step 6. Processing then continues at a step 7.

If a spot is not located, processing also continues at step 7. In step 7, the entire captured image is searched for spots using high sensitivity and shape characteristics. By high sensitivity is meant a sensitivity that is higher than a first or "normal" sensitivity used in step 4. A number of parameters affect the sensitivity of the search of an image. One parameter is the height which a point must be above the background in order to identify that point as a maxima. A second parameter is the allowable distance between spot centers for identifying a maxima. To increase sensitivity, the height above the background for a maxima is reduced, that is, the difference between the maxima and the background is reduced. To increase sensitivity, the distance between spot centers for maxima is also reduced. To obtain optimal results it may also be necessary to vary the distance between spots across or from top to bottom in a regular fashion (linear or exponential) related to the spot separation. If sensitivity is increased too much, then it is not possible to separate real maxima from noise. For example, it would not be acceptable to have a sensitivity that identified one pixel higher than surrounding pixels as a spot. It would be readily apparent to one of skill in the relevant art how to adjust sensitivity between a normal sensitivity and a higher sensitivity.

By increasing the sensitivity, more spots are located. However, increasing the sensitivity too much can introduce unwanted noise. Therefore, the present invention couples increased sensitivity with shape characteristics. A number of parameters can be used to define a shape characteristic. One such parameter is a smoothly shaped boundary. The curvature of the boundary is integrated to determine how the points of curvature are changing. Using a smoothly shaped boundary as a shape characteristic, a perfect circle would have a shape characteristic of one (1). If the spot was not a perfect circle, its shape characteristic would be a value less than about one. The smaller the value of the shape characteristic, the less smooth is the boundary of the spot. If a potential spot has a shape characteristic that is less than about 0.5, then it will not qualify as a spot based on shape in step 7. For example, a potential spot shaped as an ellipse would have a shape characteristic approximately equal to about 0.8. Because about 0.8>0.5, the elliptical potential spot would qualify as a spot based on shape in step 7. As another example, a potential spot having an elongated and thin shape (like a streak on the gel image) would have a shape characteristic approximately equal to 0.1. Because 0.1<0.5, the elongated and thin potential spot would not qualify as a spot based on shape in step 7.

In a decision step 8, it is determined whether a spot is located during the search in step 7. If a spot is located, then the spot is added to the spot list in a step 9. Processing then continues at a step 10.

If a spot is not located in step 8, processing also continues at step 10. In step 10, the processed image is presented to an operator for editing. Such editing can include, for example, separating two very big spots that are close together that have been identified as one spot. The operator then edits the image to divide the spot into the appropriate number of spots. The editing required at this step is only that necessary to generate the spot list for the captured image. This provides the necessary data for the captured image (e.g., position and IOD % of the spots) so that the captured image can be further analyzed and interpreted in accordance with the remaining steps in the method of the present invention. The processing of the captured image to generate an image file and an associated image data file is complete at an end step 11.

Figure 3:
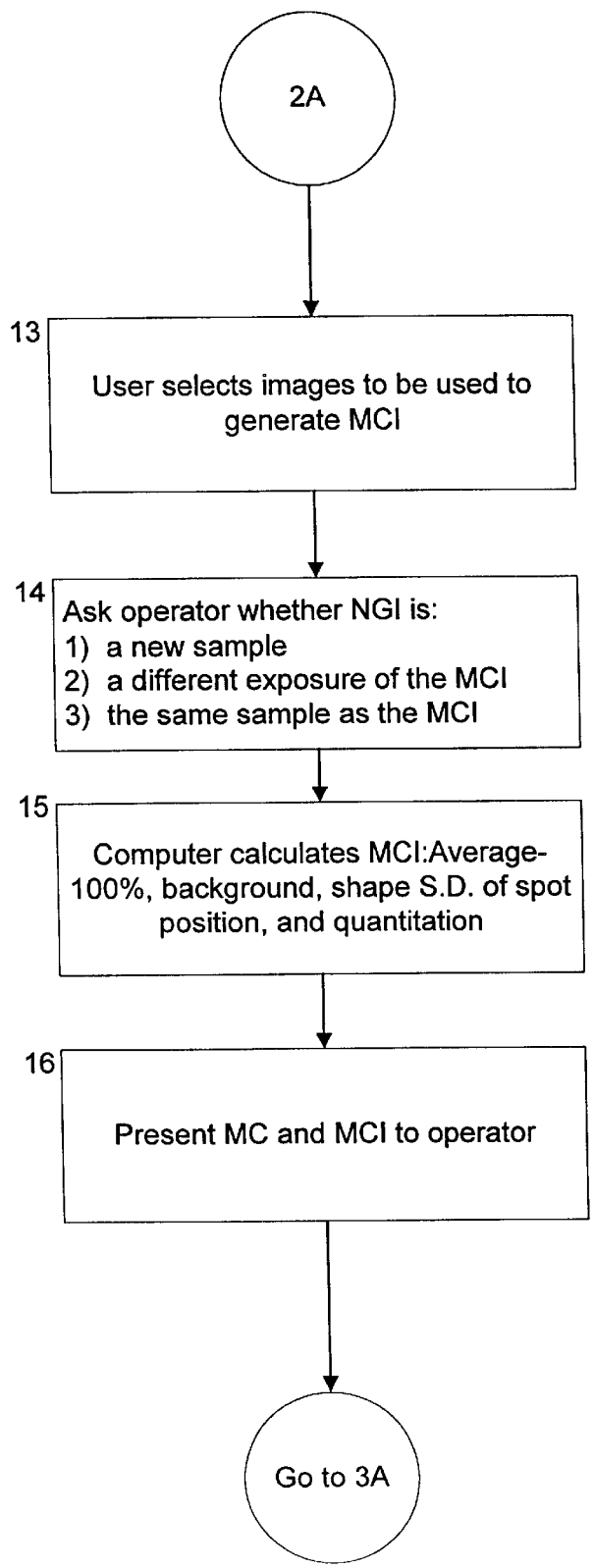
FIG. 3 shows a block diagram illustrating one embodiment for carrying out step 120 shown in FIG. 1.
Figure 4A:
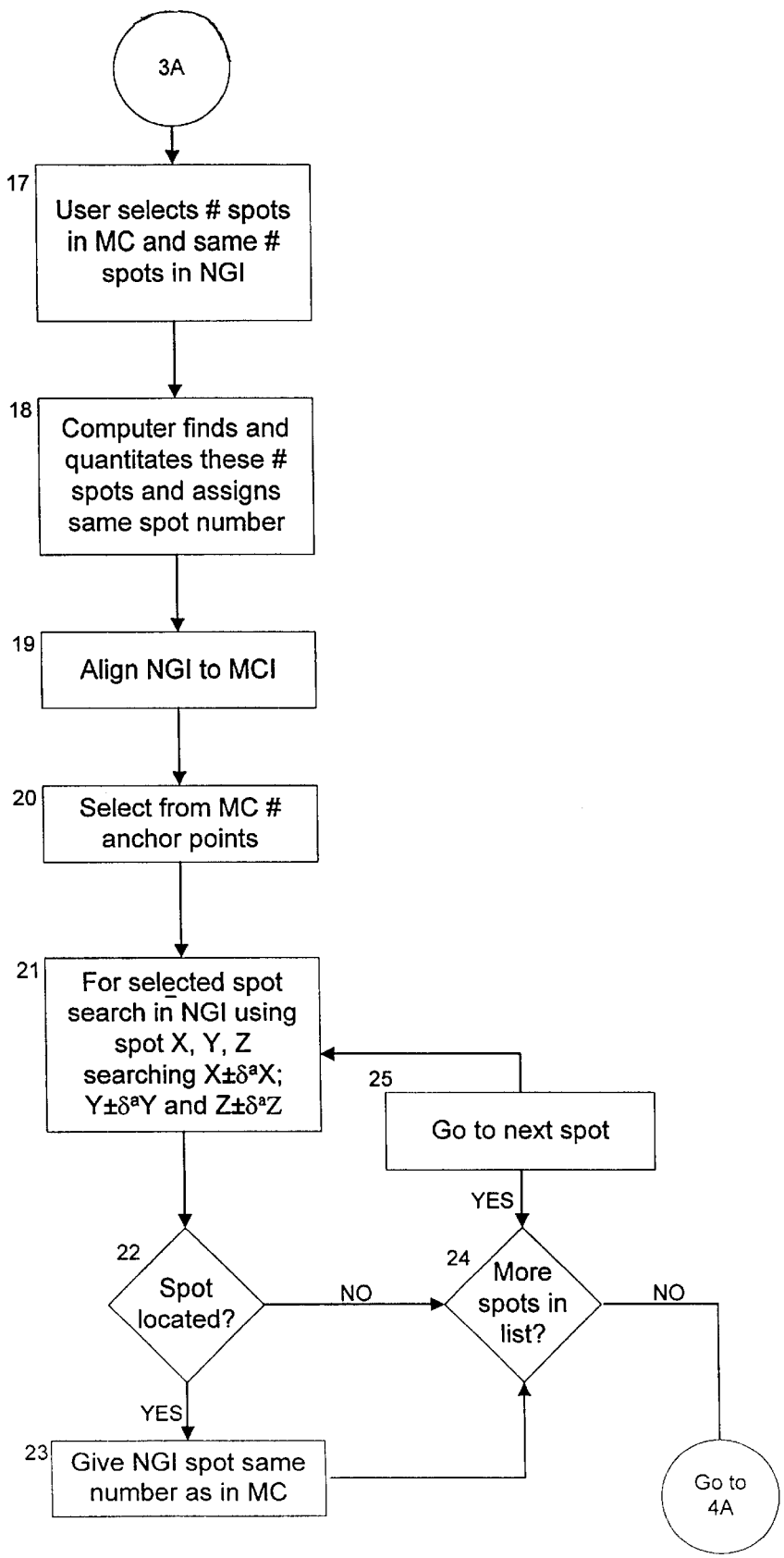
FIG. 4A and FIG. 4B show a block diagram illustrating one embodiment for carrying out steps 130 and 140 in FIG. 1.
Figure 4B:
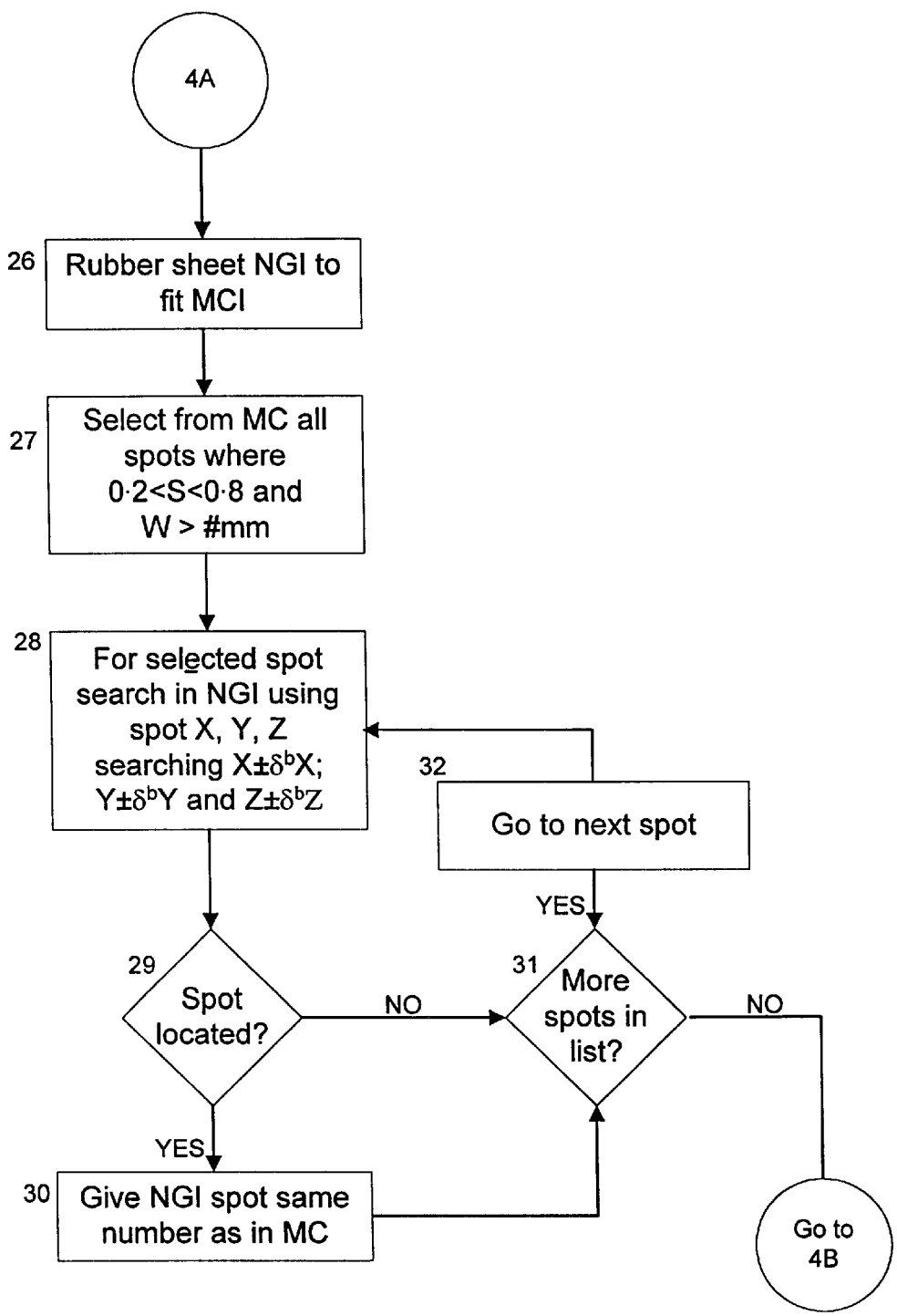

With reference now to FIG. 3, a block diagram is shown that illustrates one embodiment for carrying out step 120. Processing continues at a step 13 from step 12 in FIG. 2 by way of flow chart connector 2A. In step 13, the operator selects the image or images that will be used to generate the master composite image (MCI). As explained in the overview above, the images selected by the operator to generate the MCI generally will be those related to the particular project or experiment that the operator is conducting. For example, a operator could be conducting an experiment to compare two groups of gel images: one group of gel images relating to untreated or normal cells; and a second group of gel images relating to treated or stimulated cells. The operator would then know whether the new gel image to be interpreted was for untreated or treated cells. The operator could then appropriately select the images that will be used to generate the master composite image, i.e., untreated images for the new gel image of untreated cells and treated images for the new gel image of treated cells.

Similarly, if the operator was going to match either two exposures of the same gel or two gels of the same sample, then he or she would select either the correct image to generate the MCI.

In a step 14, the operator is then asked to select what type of analysis is to be performed, i.e., whether (1) the NGI is a new sample, (2) the NGI is a different exposure of the same gel as the MCI, or (3) the NGI is the same sample as that selected for the MCI at a different concentration. This selection causes the computer to use different "tolerance values" in the ensuing analysis. Thus, for example, if option (1) is selected: normal delta X, delta Y and delta Z values are used (e.g., delta X=1 mm, delta Y=1 mm, delta z=20%). If option (2) is selected: delta (X and delta Y values are extremely small (e.g., delta X=0.1 mm, delta Y=0.1 mm) because the images are from the same gel, but the delta Z values used are larger (e.g., delta Z=50%) because the exposures are different. If option (3) is selected, the delta X and delta Y values are normal (e.g., delta X=1 mm, delta Y=1 mm) because the gels are different but the delta Z values used are larger (e.g., delta Z=50%) because different protein loads have been applied to the gel. Henceforth, examples of the tolerance values for selection 1 are given in the text and those for selections (2) and (3) are given in brackets together with explanatory text).

If the operator selects "3," then he or she is asked how much protein was applied to the gel (and also how much protein was applied to the MCI if this is not entered into the computer already).

In a step 15, the master composite image is calculated by averaging a set of selected images (preferably two or more) that are selected by the operator. The master composite image contains a plurality of master composite spots, each master composite spot having an IOD % and a position. As used herein the "position" of a spot can be expressed using any suitable reference system. One such suitable reference system is a Cartesian-type coordinate system (rectangular parallel coordinates) in which a position is defined in terms of an "X" coordinate and a "Y" coordinate in a paired fashion (X,Y). Another suitable reference system is a polar coordinate reference system in which a position is defined in terms of an angle "θ" with respect to an axis, and a non-negative radius "r" in a paired fashion (r, θ).

Each selected image in the set has a background and corresponding spots that correspond to corresponding spots in the other selected images. An average IOD %, average background, average physical shape, standard deviation (SD) of spot position (how variable the spot position is), and/or standard deviation of the spot quantitation (how variable the spot expression level is), and the saturation value (corresponding to the numerically averaged saturation values for each of the spots) are computed from the set of selected images to generate the MCI. One or more of these values will be needed to interpret the new image.

If the operator only selects one gel for the MCI set, default values are used for the standard deviation values for spot position and spot quantitation.

To average the set of selected images, an average composite background is computed from the background of the set of selected images. The IOD % of corresponding spots in the set of selected images are averaged to form an average composite IOD % for each master composite spot in the master composite image. A physical shape of corresponding spots in the set of selected images is averaged to form an average physical shape for each master composite spot. The spot position of corresponding spots in the set of selected images are averaged to form an average spot position for each master composite spot. For each master composite spot, a standard deviation for the average composite IOD % is computed, along with a standard deviation for the average spot position, and the saturation value (corresponding to the numerically averaged saturation values for each of the spots).

A master composite (MC) corresponding to the master composite image is also generated. The master composite contains image data, such as in a tabular form, that is associated with the master composite image. The master composite comprises the position, the IOD %, a spot number, and a saturation value (S) for each master composite spot in the master composite image. As will be described in more detail below, saturation value S is used to select spots from the master composite that have particular saturation values.

The master composite can also include the molecular weight (MW) and the isoelectric point (pI) for the proteins corresponding to the master composite spots.

The MC and MCI are presented to the operator in a step 16. This allows the operator to do a review of the MC and the MCI, and confirm that the analysis and interpretation of a new gel image (NGI) should proceed. Processing continues by way of flow chart connector 3A to a step 17, shown in FIG. 4A.

In step 17, the operator selects a number (#) of spots that are present in both the MCI and in the NGI. To facilitate selection of the spots by the operator, both the MCI and the NGI gel patterns are displayed for the operator. The spots selected in step 17 function as common anchor points for aligning the NGI with the MCI. The common anchor points, being spots present in both the MCI and the NGI, assist in getting the two images aligned with each other. The common anchor points are used to mathematically slide and rotate the two images with respect to one another so that the common anchor points are lined up.

Each common anchor point corresponds to a new image common anchor spot in the NGI and to a master composite common anchor spot in the MCI. Preferably, three common anchor points are selected by the operator in step 17. However, other numbers of common anchor points can be used. Alternatively, a single common anchor point can also be used.

In a step 18, the new image common anchor spot, that corresponds to each common anchor point, is located in the NGI and its position determined. The master composite common anchor spot is located in the MCI and its position and its spot number are determined. A spot number is assigned to the new image common anchor spot that is the same as the spot number for the corresponding master composite common anchor spot.

In a step 19, the NGI is aligned with the MCI. A position correction is applied so that the position of the new image common anchor spot is aligned with the position of the master composite common anchor spot. The position correction corrects the (X,Y) position of the new image common anchor spot so that it is aligned with the position of the master composite common anchor spot. The position correction thus determined is applied to the (X,Y) position of every pixel in the NGI to align the NGI with the MCI. From step 19 through step 78, further input or intervention from an operator is not required.

In step 20, a number (#) of anchor points is selected from the MC. The spots selected in step 20 function as primary anchor points for aligning the NGI with the MCI. The master composite is searched to identify a predetermined number of primary anchor points. Preferably, fifty (50) primary anchor points are used, but other numbers of primary anchor points can be used, less than about 3–500 or any range or value therein, such as about 5–20, 20–30, 30–60, 60–200 or 200–500.

The primary anchor points are selected so that each of the primary anchor points is separated from the other primary anchor points by a least a predetermined separation threshold. The predetermined separation threshold can be, for example, about 1–200 mm, such as about 10–40 mm. A preferred separation is 20 mm.

The primary anchor points are selected to each have a saturation value S that falls within a predetermined saturation value range. The predetermined saturation value range can be, for example, about 0.2<S<0.8. Primary anchor points would then not contain any pixels having a saturation value outside this range. This is done so that the primary anchor points are not saturated spots or weak spots. If a spot contains some saturated pixels, it should not be used as an anchor point. This is because the saturation of the spot makes it more difficult to determine the spot center for the spot. It can also be inaccurate to determine the correct center for weak spots because electronic noise can "shift" the position of the darkest pixel. A spot center position can also be calculated using the spot shape characteristics, as known in the art or as described herein. A spot whose spot center is not reliably known should not be used as an anchor point for aligning images. Additionally, scanning devices used to scan images into a computer tend not to be linear at high and low optical densities. By selecting saturation values between about 0.2 and about 0.8 the linearity problems associated with high and low (saturated and weak, respectively) optical densities is avoided.

The primary anchor points can also be selected using a standard deviation percentage (SD %) for (X,Y) or for the average composite IOD % (Z). The SD % represents the standard deviation of the spot divided by the average X, Y, or Z (IOD %) for that spot, multiplied by 100%. For example, the primary anchor points can be selected so that an SD % for IOD % is less than about 40%.

As another example, 10–2000 spots with the best X, 10–2000 spots with the best Y, and 10–2000 spots with the best Z are chosen. It is then determined whether the chosen spots are sufficiently separated. For spots that are too close together, the spot with the largest sum of SD %X and SD %Y is discarded. This process is repeated until the desired number of spots, e.g., 1–1000 are chosen.

In a step 21, the NGI is searched for each of the anchor points selected in step 20 using the (X,Y) position of the anchor point and the IOD % (Z) of the anchor point. For each anchor point in the set of anchor points, an X position coordinate, a Y position coordinate, the IOD %, and the spot number are determined. This information can be obtained from the MC (the anchor points selected in step 20 are selected from the MC). For each anchor point in the set of anchor points, the new image is searched in a region defined by $X \pm \delta^a X$ and $Y \pm \delta^a Y$. $\delta^a X$ is an X position coordinate tolerance and $\delta^a Y$ is a Y position coordinate tolerance for the (X,Y) position of the anchor point. Preferably, $\delta^a X$ and $\delta^a Y$ are each equal to 1 mm. However, $\delta^a X$ and $\delta^a Y$ do not have to be equal to each other. The region defined by $X \pm \delta^a X$ and $Y \pm \delta^a Y$ is searched to locate a new image spot that has an IOD % (Z) that is equal to the IOD % of the anchor point ± an IOD % tolerance. This is expressed as $Z \pm \delta^a Z$, with $\delta^a Z$ being the IOD % tolerance. Preferably, the IOD % tolerance is 0.1–50, e.g., 1–20, 5–20, 10–30, 30–50, or 25–35%.

If a new image spot is located in the NGI in the search in step 21 (there is a spot in the NGI that corresponds to the anchor point) as determined in a decision step 22, then the located new image spot is assigned a spot number that is the same as the spot number for the anchor point in a step 23. The located new image spot and its corresponding anchor point are then considered to be "matched". The matched anchor point is then removed from the list of anchor points to be searched. The matched anchor point is also removed from the master composite spots that remain to be matched to spots in the new gel image. Processing then continues at a step 24.

If a new image spot that corresponds to the anchor point is not located in the NGI, then processing also continues at step 24.

In step 24, it is determined if there are more anchor points to search for. If there are no more anchor points to search for, then processing continues at a step 26 in FIG. 4B by way of flow chart connector 4A. If it is determined in step 24 that there are more anchor points to search for, then the next anchor point is selected in a step 25. Processing then continues at step 21 until all anchor points in the set of anchor points have been searched for in the new gel image.

In step 26, the NGI is "rubber sheeted" to fit the MCI. As known to one of skill in the relevant arts, rubber sheeting is an image processing term whereby the pixel positions of an image are given vectors that are distorted to produce a "distorted" rubber sheeted image. The rubber sheeting process is done for display and spatial calculation purposes only. The raw gray level data associated with each pixel remain unchanged. Visually, rubber sheeting is akin to distorting a picture on a sheet of rubber or latex, such as on a balloon. When the balloon is pulled, the picture is stretched or distorted.

To rubber sheet the NGI to fit the MCI, the (X,Y) coordinates of all pixels in the NGI are corrected by another position correction so that the new image common anchor spots in the NGI fit geometrically over the corresponding master composite common anchor spots (see above discussion with respect to steps 17–19). The rubber sheeting process uses the common anchor points (corresponding to the new image common anchor spots in the NGI and to the master composite common anchor spots in the MCI) to provide justification between the two images (NGI and MCI). The rubber sheeting process is performed periodically throughout the method of the present invention to improve the alignment of the NGI and the MCI throughout the analysis and/or interpretation of the NGI. The repeated rubber sheeting is necessary because of the elasticity and variability of the gel medium from which both the NGI and the MCI are derived.

In a step 27, spots are selected from the master composite that have a particular saturation value S and a particular distance W between spot centers. Master composite spots are selected from the MC that have a saturation value S so that about 0.2<S<0.8 to form a first set of selected master composite spots. This first criteria based upon saturation value avoids spots that are too strong or too weak. Strong and weak spots are not reliable anchor points because it is difficult to find the spot center. A spot that is too strong is saturated at the center. It is difficult to find the center of the spot because the spot is all black over a number of pixels. A spot that is too weak is susceptible to having electronic noise artificially move the center of the spot.

From this first set of selected master composite spots, a set of secondary anchor points is selected so that each selected master composite spot in the set of secondary anchor points is separated from the other selected master composite spots in the set of secondary anchor points by a distance W that is greater than a predetermined number (#) of mm. This ensures that the spots selected for secondary anchor points are not too close together. Preferably, W is greater than 3 mm.

In an alternate embodiment, W increases from the top of the gel image to the bottom of the gel image. This would compensate for the fact that spots are very small at the top of a gel image and large at the bottom of a gel image. In yet another embodiment, W can be a operator-defined variable that could be set for each new gel image being interpreted.

In a step 28, the NGI is searched for each of the secondary anchor points selected in step 27 using the (X,Y) position of the secondary anchor point and the IOD % (Z) of the secondary anchor point. For each secondary anchor point in the set of secondary anchor points, an X position coordinate, a Y position coordinate, the IOD %, and the spot number are determined. This information can be obtained from the MC (the secondary anchor points selected in step 27 are selected from the MC). For each secondary anchor point in the set of secondary anchor points, the new image is searched in a region defined by $X \pm \delta^b X$ and $Y \pm \delta^b Y$. $\delta^b X$ is an X position coordinate tolerance and $\delta^b Y$ is a Y position coordinate tolerance for the (X,Y) position of the secondary anchor point. Preferably, $\delta^b X$ and $\delta^b Y$ are each equal to 0.5 mm. However, $\delta^b X$ and $\delta^b Y$ do not have to be equal to each other. The region defined by $X \pm \delta^b X$ and $Y \pm \delta^b Y$ is searched to locate a new image spot that has an IOD % (Z) that is equal to the IOD % of the secondary anchor point ± an IOD % tolerance. This is expressed as $Z \pm \delta^b Z$, with $\delta^b Z$ being the IOD % tolerance. Preferably, the IOD % tolerance is 20%.

The tolerance values $\delta^b X$ and $\delta^b Y$ can be smaller than the tolerance values $\delta^a X$ and $\delta^a Y$ (see step 21) because the rubber sheeting process conducted in step 26 has aligned the NGI more closely to the MCI so that a smaller position region has to be searched to locate the desired spot.

However, $\delta^b Z$ can be the same as $\delta^a Z$ because the rubber sheeting process only affects positional alignment, and does not affect the quantitation represented by Z (IOD %).

If a new image spot is located in the NGI in the search in step 28 (there is a spot in the NGI that corresponds to the secondary anchor point) as determined in a decision step 29, then the located new image spot is assigned a spot number that is the same as the spot number for the secondary anchor point in a step 30. The located new image spot and its corresponding secondary anchor point are then considered to be "matched". The matched secondary anchor point is then removed from the list of secondary anchor points to be searched. The matched secondary anchor point is also removed from the master composite spots that remain to be matched to spots in the new gel image. Processing then continues at a step 31.

If a new image spot that corresponds to the secondary anchor point is not located in the NGI, then processing also continues at step 31.

Figure 5:
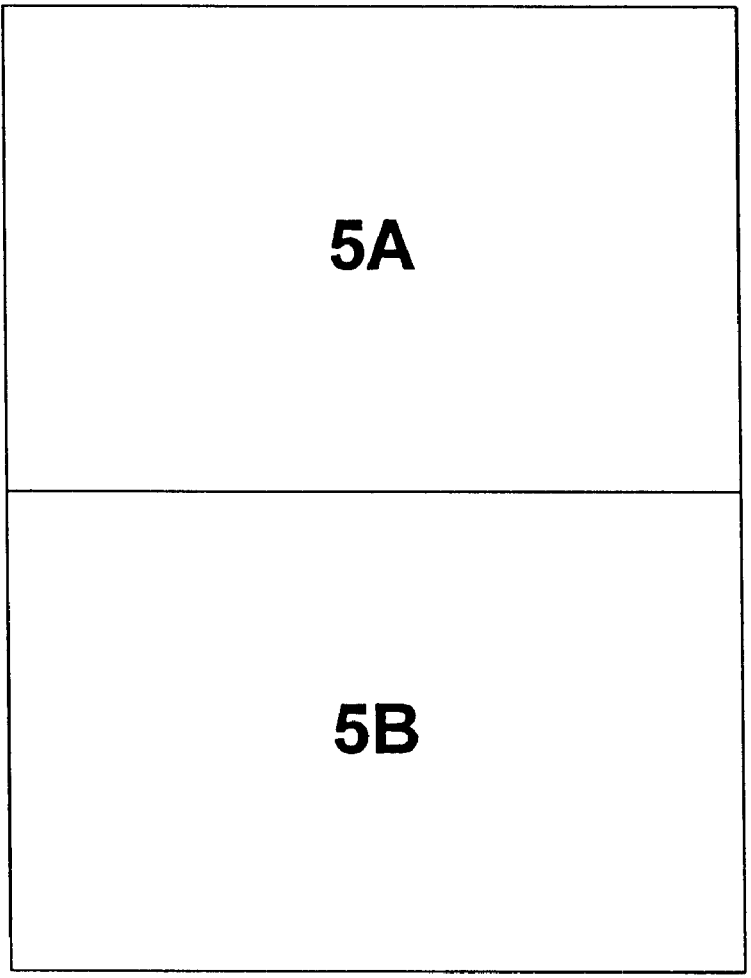
FIG. 5 shows the orientation for FIGS. 5A and 5B.
Figure 5:
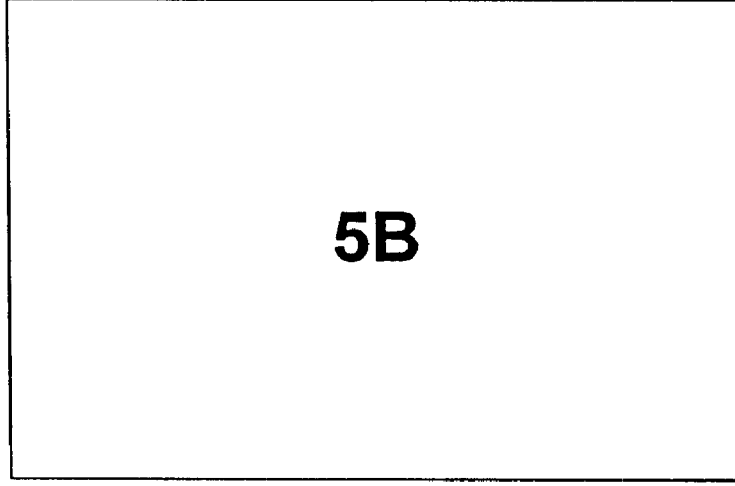
Figure 5A:
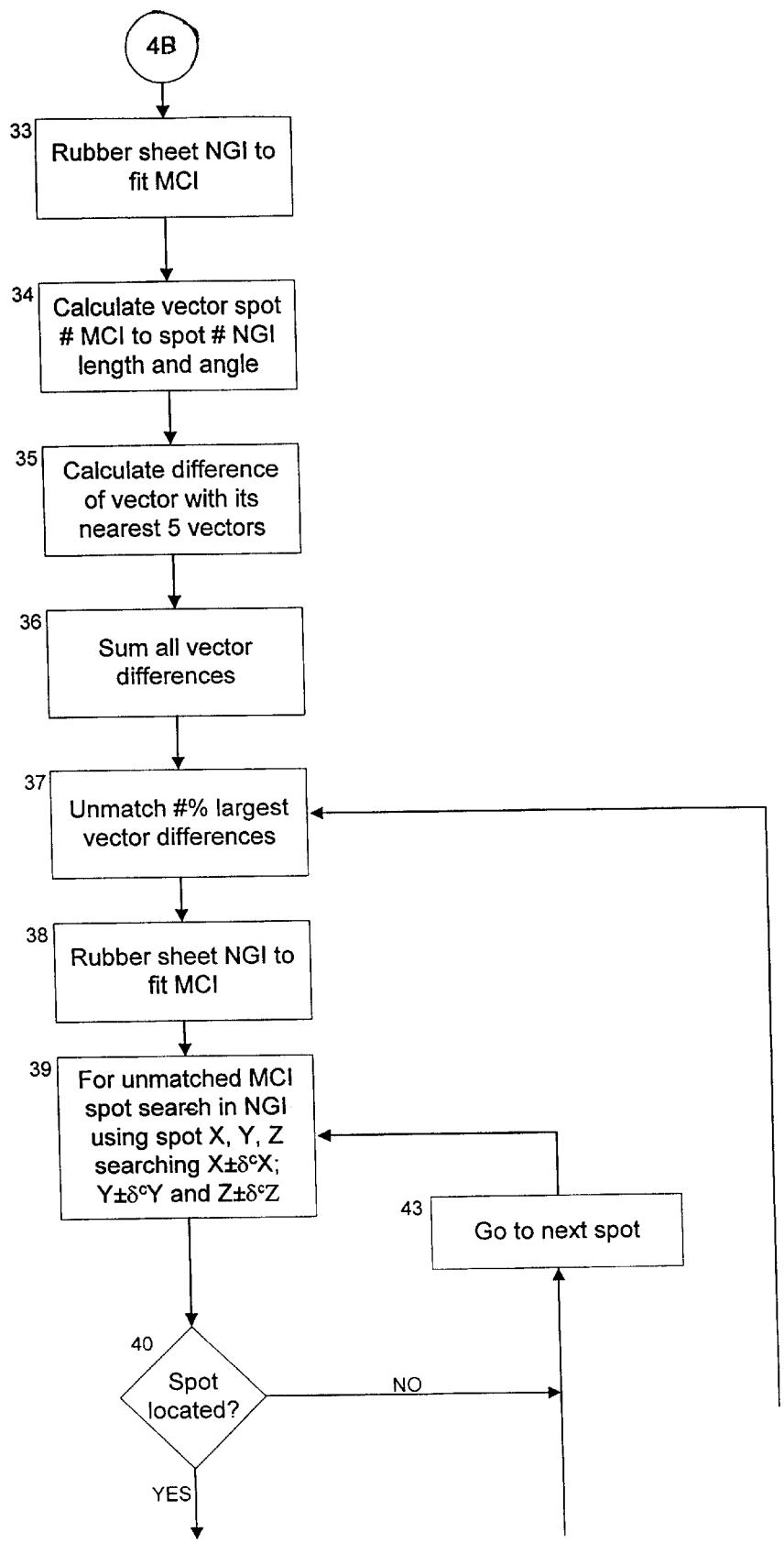
FIG. 5A and FIG. 5B show a block diagram illustrating one embodiment for carrying out step 150 in FIG. 1.

In step 31, it is determined if there are more secondary anchor points to search for. If there are no more secondary anchor points to search for, then processing continues at a step 33 in FIG. 5A by way of flow chart connector 4B. If it is determined in step 31 that there are more secondary anchor points to search for, then the next secondary anchor point is selected in a step 32. Processing then continues at step 28 until all secondary anchor points in the set of secondary anchor points have been searched for in the new gel image.

In step 33, the new gel image is again rubber sheeted to fit the master composite image. This step is carried out in the same manner as described above for step 26.

Steps 34–48 (FIGS. 5A and 5B) are carried out to perform a quality control check on the matches that have been made up to this point in the process between spots in the NGI and anchor points in the MCI. Each match that is made forms a pair of matched spots—a spot in the NGI is matched to a corresponding anchor point in the MCI. Each spot in a pair of matched spots has the same spot number. That is, when a spot is located in the NGI that matches a corresponding anchor point in the MCI, the matched spot in the NGI is assigned the same spot number as its match or corresponding anchor point in the MCI. NGI spots that are matched are placed in a set of matched new image spots. For each pair of matched spots, a vector is created. The base of the vector is on the MCI anchor point of the matched pair. The vector extends from the MCI anchor point of the matched pair to the NGI spot of the matched pair. This vector has a length, and an angle that is measured relative to the base on the MCI anchor point. Alternatively, the angle could be measured relative to the end of the vector opposite to the base, that is, relative to the NGI spot. Such an alternative measurement would produce an angle that differed by 180 degrees from an angle measured relative to the MCI anchor point. In step 34, the length and angle of each matched pair vector (the vector for each matched pair) are calculated. Spots which lie on the edge of the gel cannot have five other matched pairs lying around them. Therefore, one has to compensate for this either by omitting these spots from the analysis or by extrapolating the tendency of the vectors as they come up to the edge spot.

In a step 35, the difference between the matched pair vector and its nearest five vectors is computed for each matched pair vector. Preferably, five vectors are used in step 35, although other numbers of vectors could be used. The length and angle of the five nearest vectors to each matched pair vector are computed. The vector length of the five nearest vectors are averaged to form an average nearest vector length. The vector length of the matched pair vector is subtracted from the average nearest vector length to form a vector difference for each matched pair. A set of vector differences is thereby created that corresponds to the set of matched new image spots. In a step 36, the vector differences in the set of vector differences are summed to form a vector difference sum.

If the vector difference for a matched pair is large, this indicates that a good match has not been made. The largest vector differences in the set of vector differences represent matches that should be further analyzed because a good match between NGI spots and anchor points may not have been made. In a step 37, matched pairs that correspond to a predetermined percentage of the largest vector differences within the set of vector differences are "unmatched" to form a set of unmatched new image spots. Since the distortion within a gel is usually greatest at the edges then for gel images the pairs of spots that are selected to be unmatched, (i.e., the worst matches) must be selected relative to the matches around them and not on absolute terms. Whether this is calculated by comparing within particular areas or within groups of vectors will be clear to one skilled in the art and depends on the type of images to be matched. The vector differences are analyzed to determine which vector differences fall within a predetermined percentage, for example about 10%, of the largest vector differences. The matched pairs that have a vector difference that falls within this 10% of the largest vector differences would be unmatched. The new image spots that are unmatched in step 37 are placed in the set of unmatched new image spots. Step 37 functions to remove or unmatch the worst matches that have been up to this point in the process.

The matches that were unmatched in step 37 could have been caused by an alignment or justification problem between the NGI and the MCI. Therefore, in a step 38 another rubber sheeting process is carried out to fit the NGI to the MCI. The rubber sheeting process in step 38 is carried out in the same manner described above for the other rubber sheeting steps, such as step 33.

After the rubber sheeting process, an attempt is made to "rematch" the pairs that were unmatched in step 37. In a step 39, a search is made in the NGI for the spots in the new image that were unmatched in step 37. In step 39, the NGI is searched for each of the unmatched new image spots that were unmatched in step 37 using the (X,Y) position of the corresponding unmatched anchor point in the MCI and the IOD % (Z) of the corresponding unmatched anchor point. For each unmatched new image spot (corresponding to each unmatched anchor point in the MCI) in the set of unmatched new image spots, an X position coordinate, a Y position coordinate, the IOD %, and the spot number are determined for the corresponding unmatched anchor point. For each unmatched new image spot in the set of unmatched new image spots, the new image is searched in a region defined by X±$\delta^c$X and Y±$\delta^c$Y. $\delta^c$X is an X position coordinate tolerance and $\delta^c$Y is a Y position coordinate tolerance for the (X,Y) position of the corresponding unmatched anchor point. Preferably, $\delta^c$X and $\delta^c$Y are each equal to 0.4 mm. However, $\delta^c$X and $\delta^c$Y do not have to be equal to each other. The region defined by X±$\delta^c$X and Y±$\delta^c$Y is searched to locate a new image spot that has an IOD % (Z) that is equal to the IOD % of the corresponding unmatched anchor point ± an IOD % tolerance. This is expressed as Z±$\delta^c$Z, with $\delta^c$Z being the IOD % tolerance. Preferably, the IOD % tolerance is 20%.

The tolerance values $\delta^c X$ and $\delta^c Y$ can be somewhat smaller than the tolerance values $\delta^b X$ and $\delta^b Y$ (see step 28) because the rubber sheeting process conducted in step 37 has aligned the NGI more closely to the MCI so that a smaller position region has to be searched to locate the desired spot. $\delta^c X$ and $\delta^c Y$ are preferably not as small as $\delta^a X$ and $\delta^a Y$ to prevent making a bad "re-match". However, $\delta^c Z$ can be the same as $\delta^a Z$ and $\delta^b Z$ because the rubber sheeting process only affects positional alignment, and does not affect the quantitation represented by Z (IOD %).

Figure 5B:
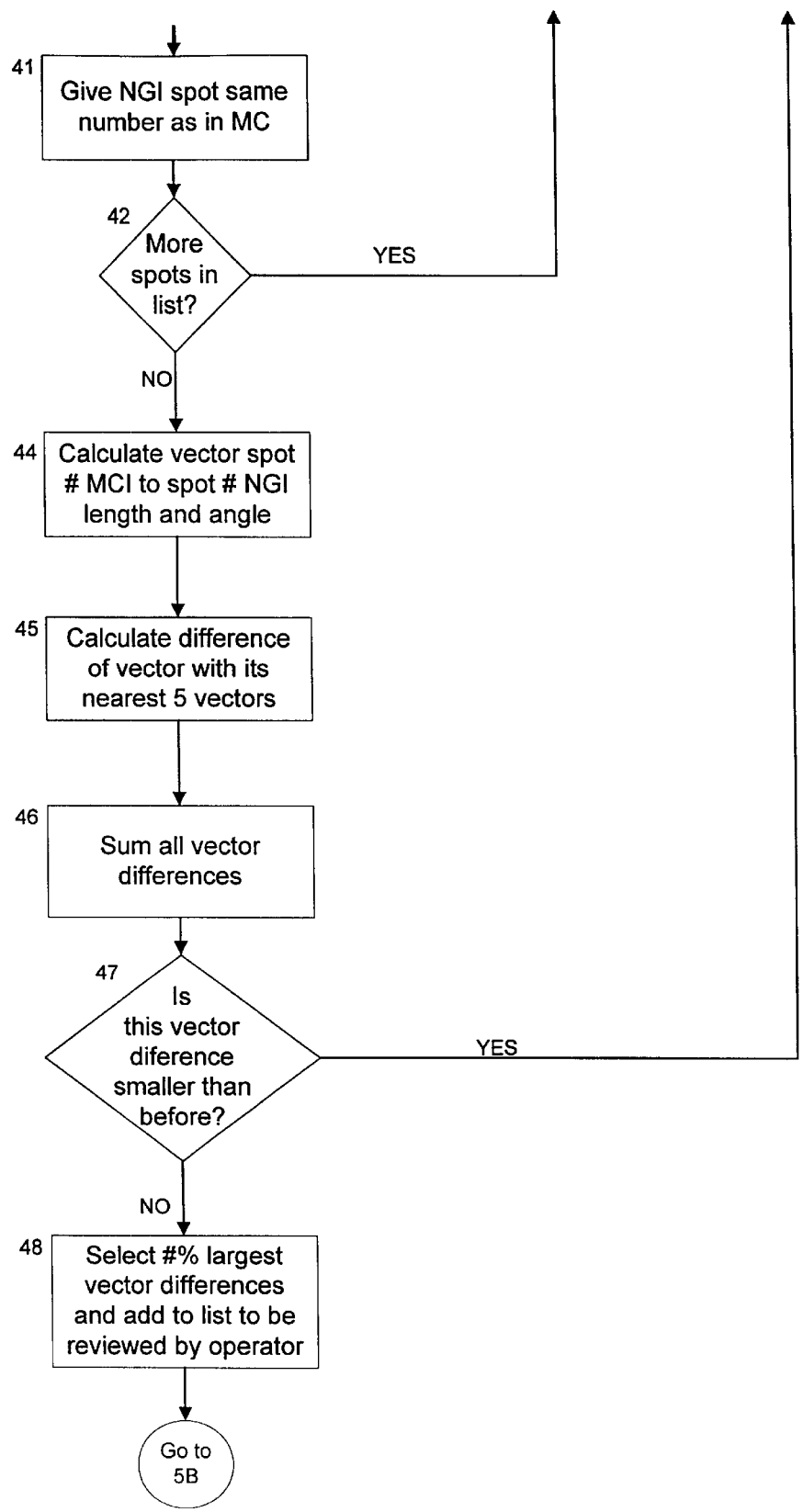
Figure 6:
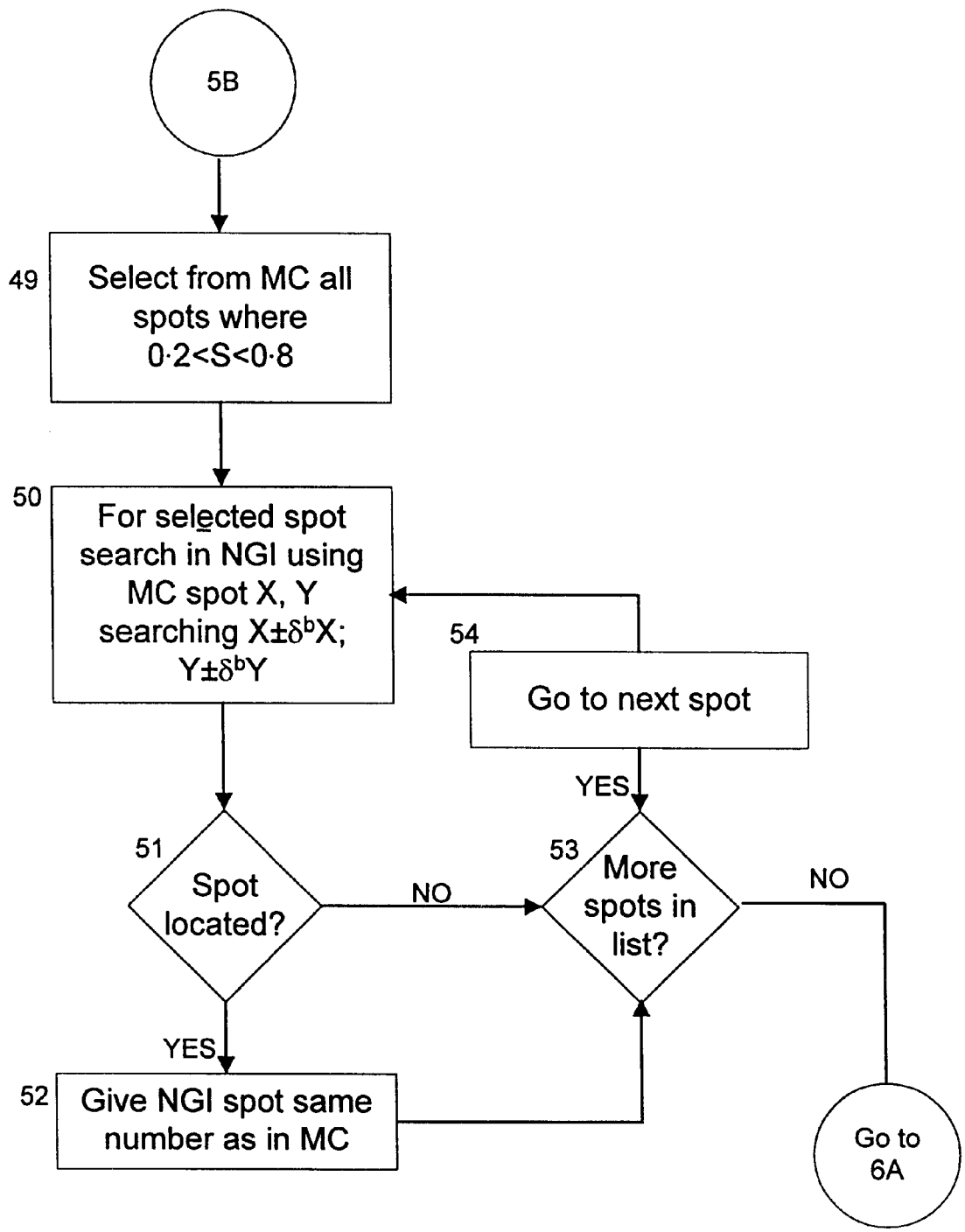
FIG. 6 shows a block diagram illustrating one embodiment for carrying out step 160 shown in FIG. 1.
Figure 7:
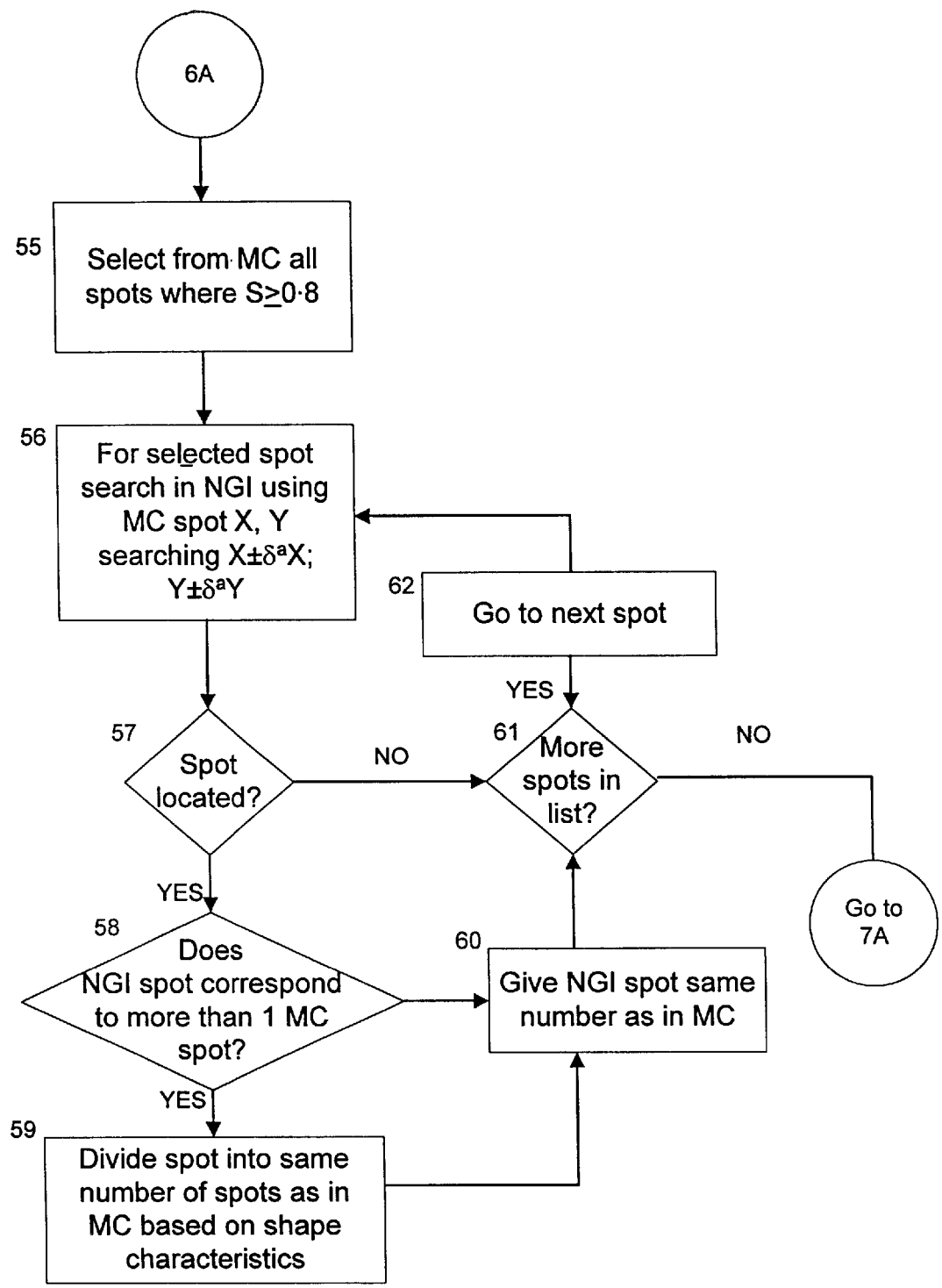
FIG. 7 shows a block diagram illustrating one embodiment for carrying out step 170 shown in FIG. 1.

If a new image spot is located in the NGI in the search in step 39 (there is a spot in the NGI that corresponds to the unmatched anchor point) as determined in a decision step 40, then the located new image spot is assigned a spot number that is the same as the spot number for the corresponding unmatched anchor point in a step 41 (see FIG. 5B). This matches the new image spot with an anchor point which may or may not be different to the one that it was matched to before. The re-matched new image spot and its corresponding anchor point are then removed from the list of unmatched spots to be searched for in step 39. The re-matched new image spot is added to the set of matched new image spots.

In a step 42, it is determined if there are more unmatched new image spots to search for. If there are more unmatched new image spots to search for, then processing continues at a step 43.

If a new image spot that corresponds to the unmatched anchor point is not located in the NGI in the search in step 39, then processing also continues at step 43. In step 43, the next unmatched new image spot is selected. Processing then continues at step 39 until all unmatched new image spots in the set of unmatched new image spots have been searched for in the new gel image.

Once all unmatched new image spots in the set of unmatched new image spots have been searched for in the new gel image, processing continues at a step 44 (see FIG. 5B). Steps 44–46 are analogous to steps 34–36 in FIG. 5A. Steps 44–46 are carried out in the same fashion as steps 34–36 to determine a second vector difference for each matched new image spot in the set of matched new image spots. The second vector differences for the matched new image spots are summed to form a second vector difference sum. In a step 47, it is determined whether the summed vector difference obtained in steps 44–46 is smaller than the summed vector difference obtained in steps 34–36. If the second vector difference sum is smaller than the first vector difference sum, then the process is closing, and good matches are being made. If the vector difference is smaller than before as determined in step 47, then the process is repeated by returning to step 37 (see FIG. 5A) to unmatch the worst matches. If the vector difference is not smaller than before as determined in step 47, then a limit to the matching process has been reached, and processing continues at a step 48.

It should be noted in the above quality control subroutine, that if unconstrained, the above process could lead in certain circumstances to the unmatching of many or all of the vectors (e.g., the possibility exists that if 10% were unmatched each time and only 9% became rematched, all the matches would eventually be unmatched). Therefore, various methods to constrain the process need to be built in. These may include but are not limited to: expressing the vector difference as a value divided by the number of matches, limiting the number of iterations of the loop, variable selection of the percentage to be unmatched (e.g., 10% first cycle, 9% second cycle, 8% third cycle and so on) and each of these may be made conditional on factors like the total number of matches (for example, if this is increasing, then no constraint is necessary) or the degree of change in the vector difference between one cycle and the next.

In addition, certain regions of the gel ma be more likely to have higher spatial variationability than others (e.g., the edges of the gel) and this might result in the gene matches (at the edges) being unmatched each time and incorrect matches in the middle of the gel being missed. Therefore, the get may have to be divided up into areas (sectors) and the unmatching process in step 38 repeated image to unmatch the worst X % within each area.

In step 48, a predetermined percentage (# a%) of the largest vector differences are selected in the same manner as discussed above for step 37 but they are not unmatched. The group of largest vector differences identified in step 48 is added to a list of items that will be reviewed by an operator once the analysis and/or interpretation of the new gel image is complete. From the vector difference on the list, the operator can locate the spot on the new gel image to determine whether the spot causing the large vector difference is a piece of dust on the gel used to generate the new gel image, or a new protein that did not appear on the master composite image. Processing then continues at a step 49 in FIG. 6 by way of flow chart connector 5B.

Steps 49–54 are carried out to detect and match well-defined spots. By well-defined spots is meant those spots that are not saturated and are not weak. As one example, well-defined spots have a saturation value S that is between about 0.2 and about 0.8. However, the saturation value for well-defined spots could vary based upon the type of image capturing device that was used to input the gel image into the computer. As noted above, scanning devices that can be used to input the data to the computer tend not to be linear at high and low optical densities. A well-defined spot should therefore have a saturation value S that is in a linear range for the type of image capturing device that was used to input the gel image into the computer.

In step 49, all master composite spots that have a saturation value S so that about $0.2 < S < 0.8$ are selected from the MC to form a set of well-defined spots. In a step 50, the NGI is searched for each of the well-defined spots selected in step 49 using the (X,Y) position of the well-defined spot. For each well-defined spot in the set of well-defined spots, an X position coordinate, a Y position coordinate, and the spot number are determined. This information can be obtained from the MC (the well-defined spots selected in step 49 are selected from the MC). For each well-defined spot in the set of well-defined spots, the new image is searched in a region defined by $X \pm \delta^d X$ and $Y \pm \delta^d Y$. $\delta^d X$ is an X position coordinate tolerance and $\delta^d Y$ is a Y position coordinate tolerance for the (X,Y) position of the well-defined spot. Preferably, $\delta^d X$ and $\delta^d Y$ are each equal to 0.1 mm. However, $\delta^d X$ and $\delta^d Y$ do not have to be equal to each other. The region defined by $X \pm \delta^d X$ and $Y \pm \delta^d Y$ is searched to locate a new image spot.

The tolerance values $\delta^d X$ and $\delta^d Y$ can be extremely small because the spatial alignment between the NGI and the MCI should be essentially perfect. This near-perfect alignment is achieved through the spatial correction and quality control process described above with reference to steps 33–48.

If a new image spot is located in the NGI in the search in step 50 (there is a spot in the NGI that corresponds to the well-defined spot) as determined in a decision step 51, then the located new image spot is assigned a spot number that is the same as the spot number for the well-defined spot in a step 52. The located new image spot and its corresponding well-defined spot are then considered to be "matched". The matched well-defined spot is then removed from the list of well-defined spots to be searched. The matched well-defined spot is also removed from the master composite spots that remain to be matched to spots in the new gel image. Processing then continues at a step 53.

If a new image spot is not located in the NGI that corresponds to the well-defined spot, then processing also continues at step 53.

In step 53, it is determined if there are more well-defined spots to search for. If there are no more well-defined spots to search for, then processing continues at a step 55 in FIG. 7 by way of flow chart connector 6A. If it is determined in step 53 that there are more well-defined spots to search for, then the next well-defined spot is selected in a step 54. Processing then continues at step 50 until all well-defined spots in the set of well-defined spots have been searched for in the new gel image.

Steps 55–62 are carried out to detect and match saturated spots. As one example, saturated spots have a saturation value S that is greater than or equal to about 0.8. However, the saturation value for saturated spots could vary based upon the type of image capturing device that was used to input the gel image into the computer. As noted above, scanning devices that can be used to input the data to the computer tend not to be linear at high and low optical densities.

In step 55, all master composite spots that have a saturation value S so that $S \geq 0.8$ are selected from the MC to form a set of saturated spots. In a step 56, the NGI is searched for each of the saturated spots selected in step 55 using the (X,Y) position of the saturated spot. For each saturated spot in the set of saturated spots, an X position coordinate, a Y position coordinate, and the spot number are determined. This information can be obtained from the MC (the saturated spots selected in step 55 are selected from the MC). For each saturated spot in the set of saturated spots, the new image is searched in a region defined by $X \pm \delta^e X$ and $Y \pm \delta^e Y$. $\delta^e X$ is an X position coordinate tolerance and $\delta^e Y$ is a Y position coordinate tolerance for the (X,Y) position of the saturated spot. Preferably, $\delta^e X$ and $\delta^e Y$ are each equal to 0.4 mm. However, $\delta^e X$ and $\delta^e Y$ do not have to be equal to each other. The region defined by $X \pm \delta^e X$ and $Y \pm \delta^e Y$ is searched to locate a new image spot.

The tolerance values $\delta^e X$ and $\delta^e Y$ are larger than $\delta^d X$ and $\delta_d Y$ because the spots centers for saturated spots are located fairly poorly. Therefore, a larger area must be searched to locate the spot center of a saturated spot.

For highly saturated spots (hereby defined as having more than 9 saturated pixels) the position of the spot centre is determined by using the spot shape characteristics. Allowances are made for cases where the saturation area covers more than one spot and the saturation area is divided up into a number of areas corresponding to the number of spots existing in the MCI and spot centres are calculated accordingly.

If a new image spot is located in the NGI in the search in step 56 (there is a spot in the NGI that corresponds to the saturated spot) as determined in a decision step 57, then processing continues at a decision step 58. If a new image spot is not located in the NGI that corresponds to the saturated spot, then it is determined in a decision step 61 if there are more saturated spots to search for. If there are no more saturated spots to search for, then processing continues at a step 63 in FIG. 8 by way of flow chart connector 7A. If it is determined in step 61 that there are more saturated spots to search for, then the next saturated spot is selected in a step 62. Processing then continues at step 56 until all saturated spots in the set of saturated spots have been searched for in the new gel image.

If a new image spot is located in the NGI that corresponds to the saturated spot in step 57, then processing continues at decision step 58. In step 58, it is determined if the located NGI spot corresponds to more than one saturated spot in the MCI. The number of spots to which the located NGI spot corresponds is determined by looking at the spot centers in the MCI. If the located NGI spot does not correspond to more than one saturated spot in the MCI, then the located new image spot is assigned a spot number that is the same as the spot number for the saturated spot in a step 60. The located new image spot and its corresponding saturated spot are then considered to be "matched". The matched saturated spot is then removed from the list of saturated spots to be searched. The matched saturated spot is also removed from the master composite spots that remain to be matched to spots in the new gel image. Processing then continues at step 61 to determine if there are more saturated spots to be processed.

If in step 58 it is determined that the located NGI spot does correspond to more than one saturated spot in the MCI, then processing continues at a step 59. In step 59, the located NGI spot is divided into a number of new image saturated spots that is equal to the number of corresponding saturated spots in the MC. For example, if it is determined in step 58 that the located NGI spot corresponds to three saturated spots in the master composite, then, in step 59, the located NGI spot will be divided into three new image saturated spots. The number of spots into which the located NGI spot is divided is determined by counting the number of spot centers in the MCI to which the located NGI spot corresponds. The shape of each divided spot in the NGI is based upon the (X,Y) positional shape of the corresponding spots in the MCI. In an alternate embodiment, the shape characteristics that are used to divide the saturated spot in the NGI could include a "Z" or IOD % shape characteristic by looking for a saddle point in the allocation of optical density in the MCI.

In step 59, one saturated NGI spot is divided to produce more than one NGI spot. Processing then continues to step 60. In step 60, each NGI spot produced or divided out is assigned the same spot number as the corresponding saturated spot in the MCI.

Figure 8:
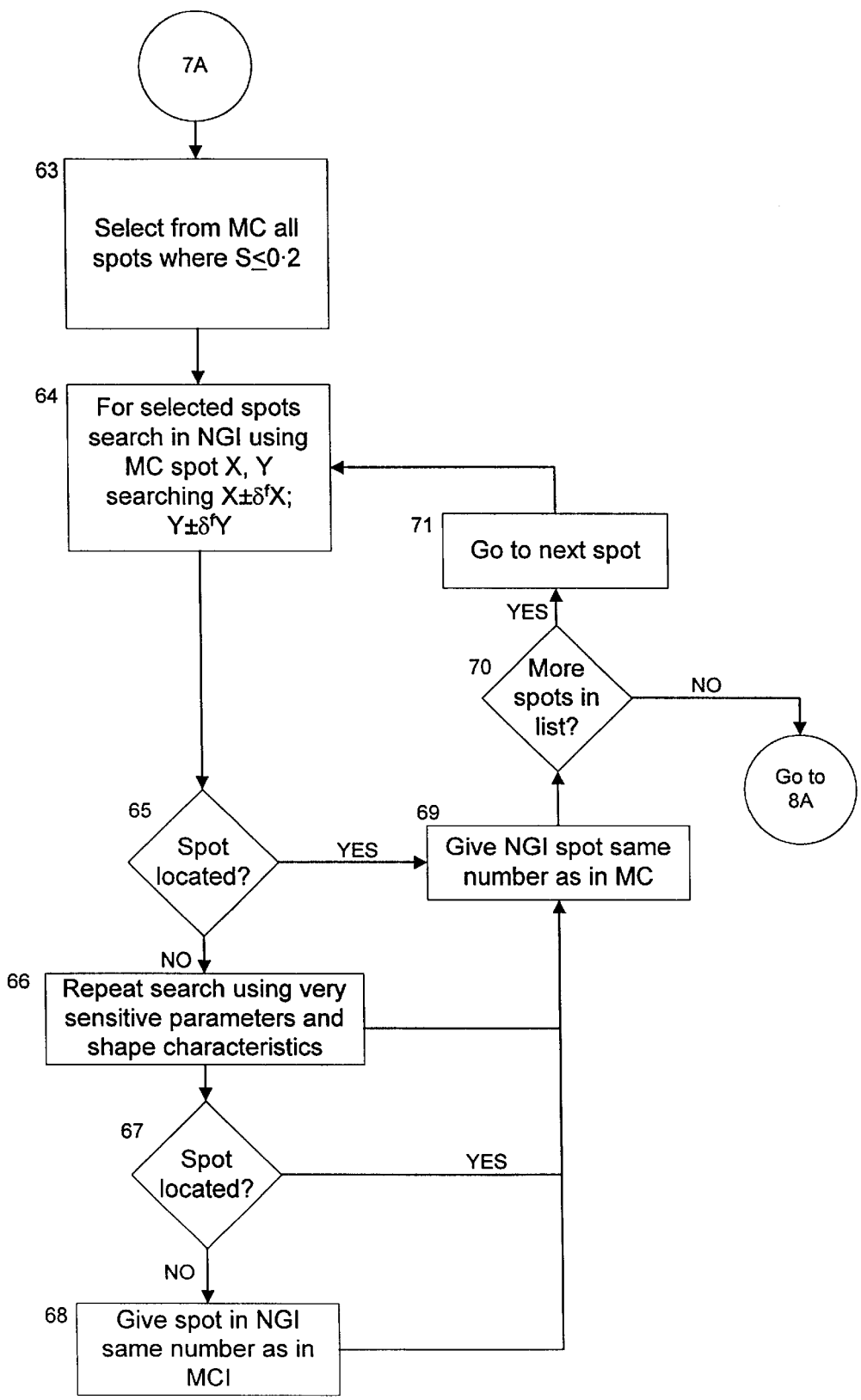
FIG. 8 shows a block diagram illustrating one embodiment for carrying out step 180 shown in FIG. 1.
Figure 9:
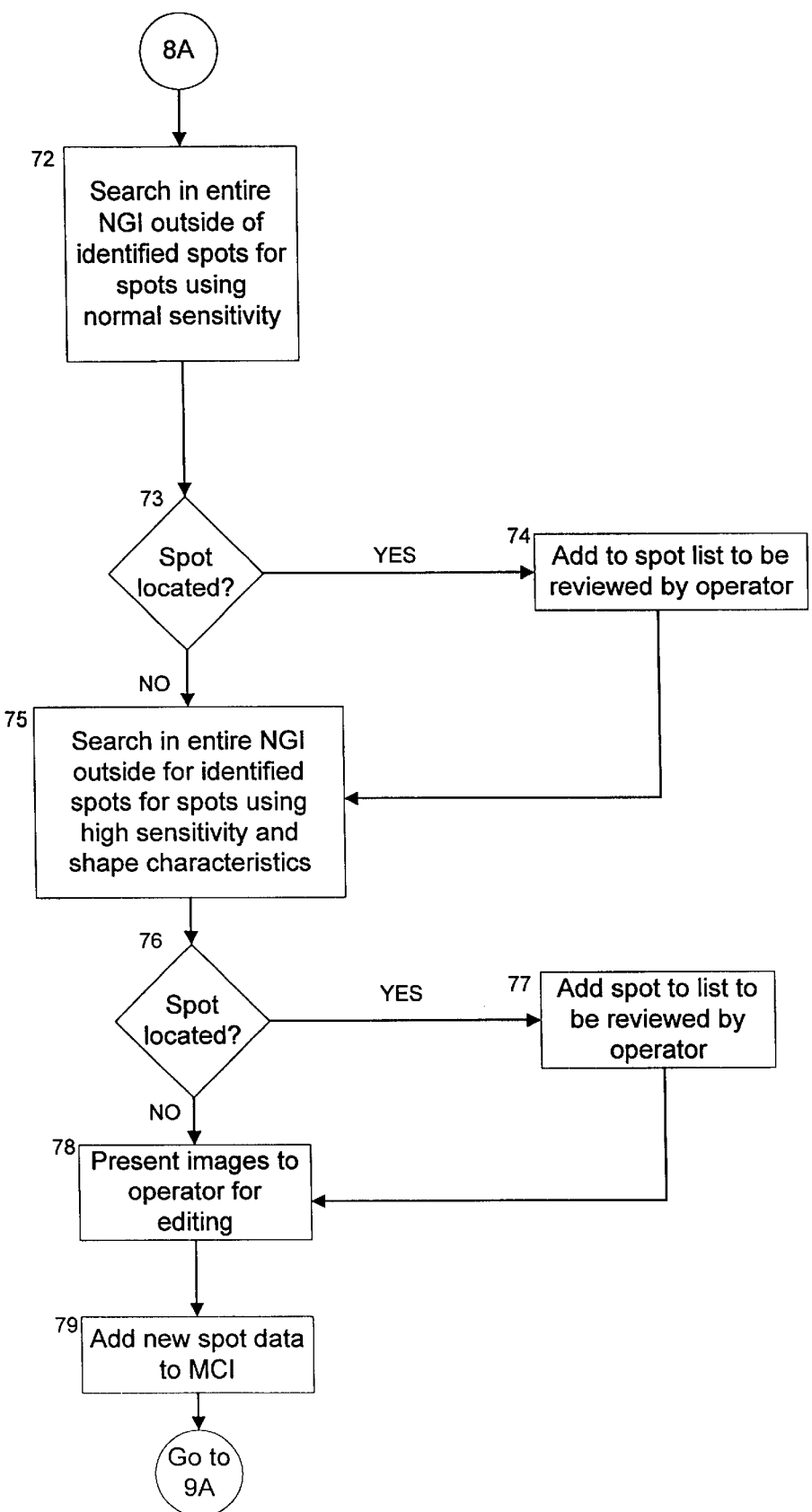
FIG. 9 shows a block diagram illustrating one embodiment for carrying out step 190 shown in FIG. 1.

With reference now to FIG. 8, processing continues at step 63 by way of flow chart connector 7A. Steps 63–71 are carried out to detect and match weak spots. As one example, weak spots have a saturation value S that is less than or equal to about 0.2. However, the saturation value for weak spots could vary based upon the type of image capturing device that was used to input the gel image into the computer. As noted above, scanning devices that can be used to input the data to the computer tend not to be linear at high and low optical densities.

In step 63, all master composite spots that have a saturation value S so that $S \leq 0.2$ are selected from the MC to form a set of weak spots. In a step 64, the NGI is searched for each of the weak spots selected in step 63 using the (X,Y) position of the weak spot. For each weak spot in the set of weak spots, an X position coordinate, a Y position coordinate, and the spot number are determined. This information can be obtained from the MC (the weak spots selected in step 63 are selected from the MC). For each weak spot in the set of weak spots, the new image is searched in a region defined by X±$\delta^f$X and Y±$\delta^f$Y. $\delta^f$X is an X position coordinate tolerance and $\delta^f$Y is a Y position coordinate tolerance for the (X,Y) position of the weak spot. Preferably, $\delta^f$X and $\delta^f$Y are each equal to about 0.2 mm. However, $\delta^f$X and $\delta^f$Y do not have to be equal to each other. The region defined by X±$\delta^f$X and Y±$\delta^f$Y is searched to locate a new image spot.

The tolerance values $\delta^f$X and $\delta^f$Y are smaller than $\delta^e$X and $\delta^e$Y because the spots centers for weak spots are located more reliably than for saturated spots. However, a very small tolerance value, less than about 0.1 mm, is not suitable because of the uncertainty in the location of spot centers for weak spots that is generated by electronic noise. Spot center position can also be calculated using spot shape characteristics.

If a new image spot is not located in the NGI in the search in step 64 as determined in a decision step 65, then processing continues at a step 66. If a new image spot is located in the NGI that corresponds to the weak spot (there is a spot in the NGI that corresponds to the weak spot), then the located new image spot is assigned a spot number that is the same as the spot number for the weak spot in a step 69. The located new image spot and its corresponding weak spot are then considered to be "matched". The matched weak spot is then removed from the list of weak spots to be searched. The matched weak spot is also removed from the master composite spots that remain to be matched to spots in the new gel image.

If a new image spot that corresponds to the weak spot is not located in the NGI, then processing continues at step 66. In step 66, the search of step 64 is repeated using very sensitive parameters and shape characteristics. The region defined by X±$\delta^f$X and Y±$\delta^f$Y is searched with a second sensitivity that is higher than the first sensitivity used to carry out the search in step 64. A shape criterion is also used to rule out those spots attributable to electronic noise. The selection of the sensitivity and shape criterion can be carried out in the same manner as discussed above with respect to step 7.

If a new image spot is not located in the NGI in the search in step 66 (there is not a spot in the NGI that corresponds to the weak spot) as determined in a decision step 66, then processing continues at a step 68. If a new image spot is located in the NGI that corresponds to the weak spot, then the located new image spot is assigned a spot number that is the same as the spot number for the weak spot in step 69. The located new image spot and its corresponding weak spot are then considered to be "matched". The matched weak spot is then removed from the list of weak spots to be searched. The matched weak spot is also removed from the master composite spots that remain to be matched to spots in the new gel image.

If a new image spot is not located in the NGI in the search in step 66, then processing continues at step 68. In step 68, a spot is added to the NGI that has the same area as the corresponding weak spot in the MCI. Every spot that exists in the MC and the MCI must be eventually located in the NGI, even if the corresponding spot located in the NGI has zero integrated optical density. If a spot in the MC cannot be found in the NGI, then a spot must be added to the NGI where the spot would be expected to be located. The spot that is added to the NGI has the same area as the corresponding spot in the MCI. In step 69, the spot added to the NGI is given the same spot number as the corresponding weak spot in the MCI. In this manner, there is a "conservation of spots" in that all of the spots in the MC are accounted for in the NGI. If a spot cannot be located in the NGI, it should be given a zero value to be accounted for statistically. The fact that the spot has "disappeared" in the NGI is a real result, and may be indicative that some treatment of the cell resulted in suppression of that particular protein. Once all spots in the MCI have been accounted for, then any additional or leftover spots in the NGI are, by definition, "new" or "unidentified" spots that could correspond to new proteins.

From step 69, processing continues at a step 70. It is determined in decision step 70 if there are more weak spots to search for. If there are no more weak spots to search for, then processing continues at a step 72 in FIG. 9 by way of flow chart connector 8A. If it is determined in step 70 that there are more weak spots to search for, then the next weak spot is selected in a step 71. Processing then continues at step 64 until all weak spots in the set of weak spots have been searched for in the new gel image.

In step 72, the entire new gel image, outside of identified or matched spots (outside of the set of matched new image spots), is searched using a normal or first sensitivity level to locate unidentified spots. The spots that have been matched or identified are set aside when conducting the search in step 72. In a decision step 73, it is determined whether a spot is located. If a spot is located in the search conducted in step 72, the located new image spot is added to the list that is to be reviewed by the operator, and processing continues to a step 75. These spots are put on the operator review list because they could represent something previously unidentified, like a new protein. The search in step 72 locates a first set of unidentified new image spots.

In step 75, the entire new gel image, outside of the set of matched new image spots and of the first set of unidentified new image spots, is searched using a high sensitivity and shape characteristics to locate a second set of unidentified new image spots. In a manner similar to that discussed previously, the high sensitivity is higher than the first sensitivity to look more closely throughout the new gel image. If a spot is located in the search conducted in step 75, as determined in a decision step 76, the located new image spot is added to the list that is to be reviewed by the operator in a step 76. Processing then continues to a step 78.

A two step search regime is used to conserve computer time and to increase the speed with which the calculations can be done. The first sensitivity search in step 72 is conducted first in order to remove some spots from the area to be searched. Searching by shape characteristics as is done in the second sensitivity search in step 75 consumes a lot of computer time. The number of spots that need to be analyzed by shape is reduced by doing a first level search at normal sensitivity.

In step 78, the new gel image and the master composite image are presented to the operator, along with the spot review list generated during the interpretation and analysis process. The operator can then determine what to do with the items on the spot review list. The items on the spot review list include the "trouble" vectors determined in step 48, as well as the "new" (unidentified) spots added in steps 74 and 77. The operator can look at the images associated with each of these items, as well as the tabular image data associated with these items. The operator can then determine whether the unidentified spots are new proteins that should be added to the MCI, as in a step 79. Processing then continues to a step 80 in FIG. 10 by way of flowchart connector 9A.

If in step 14, the operator selected either 2) a different exposure of the MCI or 3) the same sample as the MCI, then at this stage the computer carries out a correction process with a view to correcting for the limited and or non-linear response of the image capture media. Option 2) is intended for use where several exposures (usually of different lengths of time) of the same gel have been collected and option 3) is intended for use where the same sample has both cases, the ratio of the spots in the MCI and the NGI are calculated (excluding those spots which were added in steps 68 and 79 (where new spots were added to either the NGI or MCI respectively). Various methods of correction can be used but the preferred method consists of taking the highest 5% of the ratios away from the list (which may be artificially high due to electronic noise) (step 80) and then selecting the highest 10% of the remaining, step 81. The ratio of all of these spots is then averaged in step 82 (calculation of the correction factor) and the IOD values for all of the spots in the NGI are then multiplied by the correction factor in step 83.

The next state is to merge the IOD tables for these two images in step 84. For the purpose of the example described here, we will assume that this is about 0.2< saturation <0.8 but of course this will vary depending on the type of image detection and capture systems used. This is done by selecting from the MCI all spots inside the linear range of the detection systems response.

If the NGI is a stronger exposure (or a gel loaded with more sample) than the MCI then for all spots equal to or below about 0.2 saturation the values obtained from the NGI are substituted for those of the MCI.

If the NGI is a weaker exposure (or a gel loaded with less sample) than the MCI then for all spots equal to or above about 0.8 saturation the values obtained from the NGI are substituted for those of the MCI.

Finally, the %IOD for all the spots in the MCI is recalculated. In this way it is possible to extend the quantitatable region of the apparent dynamic range of the image detection system.

In an alternate embodiment, the operator can be queried to enter the molecular weight (MW) and isoelectric point (pI) for proteins on the new gel image for which this information is known. An interpolation is then carried out using the "known" MW and pI values to compute the MW and pI for the other "unknown" proteins on the new gel image for which the MW and pI are not specifically known. The MW and pI for each spot on the new gel image are added to the tabular image data (image data file) for the new gel image.

Figure 10:
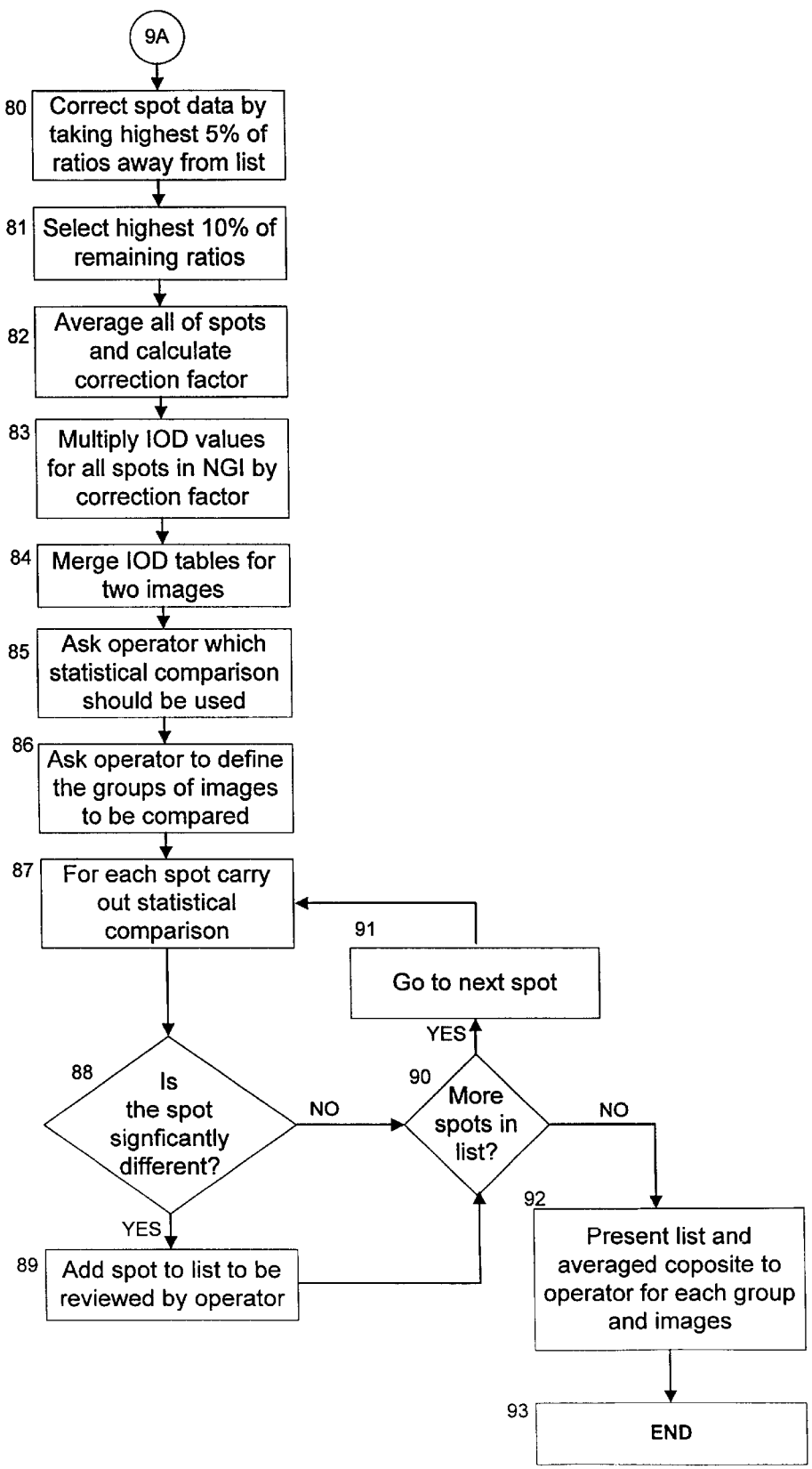
FIG. 10 shows a block diagram illustrating one embodiment for carrying out step 195 shown in FIG. 1.

Steps 85–93 in FIG. 10 are steps that are carried out so that an operator can identify changes that are relevant to an experiment or project. Steps 85–93 are directed toward the analysis of individual gel images, or groups of gel images and do not involve the use of the master composite or master composite image. The MC and the MCI were used throughout the previous steps of the process to analyze and interpret a particular new gel image.

In step 85, the operator is queried as to what statistical comparison should be used. Depending upon the statistical method used, the user may be requested at this point to enter additional data. This might be for example that in order to perform a linear regression analysis, a particular value would be assigned to each image corresponding to some measurable characteristic related to the original sample. In a step 86, the operator is asked to define the groups of images to be compared. In this manner, a first set of gel images can be compared to a second set of gel images. The first and second sets of gel images can each contain one or more gel images.

In a step 87, the statistical comparison is carried out for each spot. In a decision step 88, it is determined whether the spot is significantly different. If the spot is significantly different, then processing continues to a step 89. If the spot is not significantly different, then it is determined in a decision step 90 if there are more spots in the list to be statistically compared. If there are more spots on the list to be statistically compared, then the next spot is obtained in a step 91. Processing continues at step 87 until all spots have been statistically compared. If it is determined in step 88 that the spot is significantly different, then, in a step 89, the spot is added to a list that will be reviewed by the operator once all spots have been statistically compared.

Once all spots have been statistically compared, the list of spots is presented to the operator in a step 92. An averaged composite of tabular data for each group is presented to the operator, along with either original images, or an average composite image for each group. Processing completes at an end step 93.

The comparison process of steps 85–93 is best understood by way of the examples discussed below.

From the description of the operation of the present invention contained herein, and the associated flowcharts, it would be readily apparent to a programmer skilled in the relevant arts how to implement the present invention using a computer program that controls operation of a computer system or processor. A programmer skilled in the relevant arts could, for example, implement the method of the present invention in the C++ programming language.

3. EXAMPLES

By way of example for the comparison of steps 85–93, it may be desired to identify why three different animals, such as three individual rats, had three different blood pressures. A 2DGE gel image for artery cells from the three different animals are compared. The gels are compared to look for proteins that varied in their expression, and that could be statistically correlated with blood pressure in the animal. The type of statistical analysis would be a linear regression. The linear regression of the expression of every spot compared to the blood pressure of the animal would be carried out.

As another example, one group of gel images can relate to normal or untreated cells, such as islets. A second group of gel images can relate to treated cells, such as cells treated with interleukin (IL)-1β. The statistical average of each spot in each set of gel images is computed. The statistical average of each spot in the first set of gel images is compared to the statistical average of each spot in the second set of gel images to determine if they are statistically different. In this manner, the operator is able to quickly and easily determine what proteins are changed (either up- or downregulated) by the IL-1β treatment.

As yet another example, one group of images can relate to normal rats and another group of images to diabetic rats. The objective is to find the difference between the two groups. The gel images are divided into two sets: a first set of gel images for the normal rats; and a second set of gel images for the diabetic rats. The analysis is carried out in a similar fashion to that described above for treated and untreated islets to determine differences in protein expression between normal and diabetic rats.

4. Implementation of the Present Invention

Figure 11:
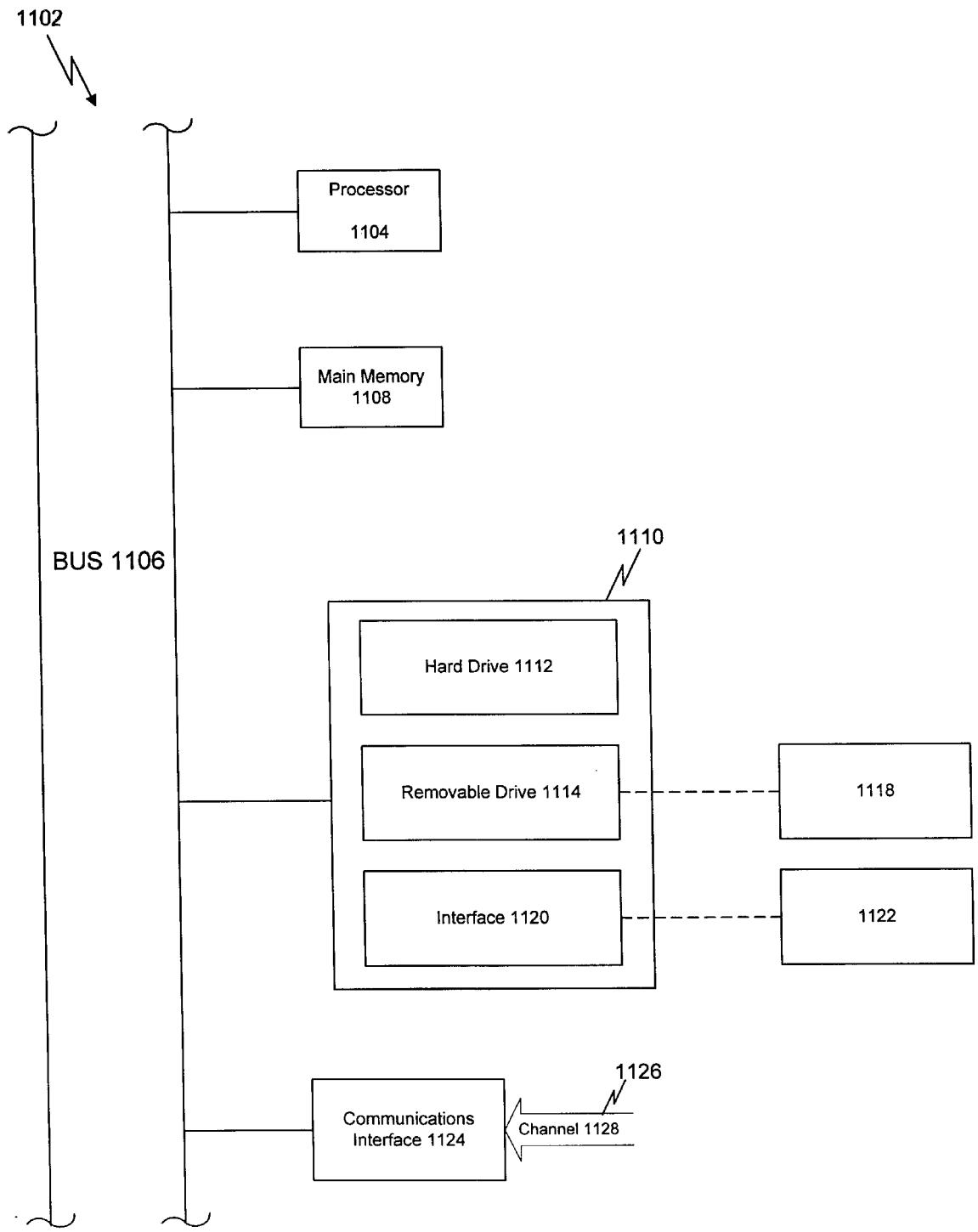
FIG. 11 shows a block diagram for an exemplary computer system suitable for use with the present invention.

As noted above, the invention may be implemented using hardware, software or a combination thereof, and may be implemented in a computer system or other processing system. In one embodiment, the invention is directed toward a computer system capable of carrying out the functionality described herein. An exemplary computer system 1102 is shown in FIG. 11. Computer system 1102 includes one or more processors, such as processor 1104. Processor 1104 is connected to a communication bus 1106. Various software embodiments are described in terms of this exemplary computer system. After reading this description, it will become apparent to a person skilled in the relevant art how to implement the invention using other computer systems and/or computer architectures.

Computer system 1102 also includes a main memory 1108, preferably random access memory (RAM), and can also include a secondary memory 1110. Secondary memory 1110 can include, for example, a hard disk drive 1112 and/or a removable storage drive 1114, representing a floppy disk drive, a magnetic tape drive, an optical disk drive, etc. Removable storage drive 1114 reads from and/or writes to a removable storage unit 1118 in a well known manner. Removable storage unit 1118, represents a floppy disk, magnetic tape, optical disk, etc. which is read by and written to by removable storage drive 1114. As will be appreciated, removable storage unit 1118 includes a computer usable storage medium having stored therein computer software and/or data.

In alternative embodiments, secondary memory 1110 may include other similar means or memory devices for allowing computer programs or other instructions to be loaded into computer system 1102. Such memory devices can include, for example, a removable storage unit 1122 and an interface 1120. Examples of such can include a program cartridge and cartridge interface (such as that found in video game devices), a removable memory chip (such as an EPROM, or PROM) and associated socket, and other removable storage units 1122 and interfaces 1120 which allow software and data to be transferred from removable storage unit 1122 to computer system 1102.

Computer system 1102 can also include a communications interface 1124. Communications interface 1124 allows software and data to be transferred between computer system 1124 and external devices (not shown), such as a scanning device for inputting gel images into computer system 1102. Examples of communications interface 1124 can include a modem, a network interface (such as an Ethernet card), a network interface suitable for interfacing with the INTERNET, a communications port, a PCMCIA slot and card, etc. Software and data transferred via communications interface 1124 are in the form of signals 1126 which can be electronic, electromagnetic, optical or other signals capable of being received by communications interface 1124. Signals 1126 are provided to communications interface via a channel 1128. Channel 1128 carries signals 1126 and can be implemented using wire or cable, fiber optics, a phone line, a cellular phone link, an RF link and other communications channels.

In this document, the terms "computer program medium," "computer program product," "program storage device," and "computer usable medium" are used to generally refer to media such as removable storage device 1118, a hard disk installed in hard disk drive 1112, and signals 1126. These computer program products provide software to computer system 1102.

Computer programs (also called computer control logic) are stored in main memory and/or secondary memory 1110. Computer programs can also be received via communications interface 1124. Such computer programs, when executed, enable the computer system 1102 to perform the features of the present invention as discussed herein. In particular, the computer programs, when executed, enable processor 1104 to perform the features of the present invention. Accordingly, such computer programs represent controllers of computer system 1102.

In an embodiment where the invention is implemented using software, the software may be stored in a computer program product and loaded into computer system 1102 using removable storage drive 1114, hard drive 1112 or communications interface 1124. The control logic (software), when executed by processor 1104, causes processor 1104 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

5. CONCLUSION

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A computer program product comprising a computer useable medium having computer program logic recorded thereon for enabling a processor in a computer system to analyze one or more two dimensional gel electrophoresis (2DGE) images, said computer program logic comprising:

(1) at least one routine for capturing a new image of an electrophoresis gel containing at affected and/or unaffected proteins, wherein said new image contains an undetermined position and integrated optical density percentage (IOD %) corresponding to each said protein;

(2) at least one routine for generating a master composite image which is used to analyze the new image, wherein said master composite image contains a plurality of master composite spots, each master composite spot being defined by at least an IOD % and a position;

(3) at least one routine for generating a master composite spot data list, wherein the master composite spot data list comprises at least a position, an IOD %, a unique spot identifier, and the variability of the spot for the position and IOD %, for each of the plurality of master composite spots;

(4) at least one routine for aligning said new image with said master composite image;

(5) at least one routine for determining the position and IOD % of new image spots corresponding to proteins using the spot data information from the master composite image to guide the search for and identification of new image spots that have a position that is within a position tolerance of the position of the corresponding master composite spots and that have an IOD % that is within an IOD % tolerance of the IOD % of corresponding master composite spots to form a set of matched new image spots corresponding to unaffected proteins;

(6) at least one routine for determining the position and IOD % of new image spots corresponding to proteins using the spot data information from said master composite image to guide the search for and identification of new image spots that have a position that is within a position tolerance of the position of the corresponding master composite spots but that have an IOD % that is outside the IOD % tolerance of the IOD % of corresponding master composite spots, to form a set of matched new image spots corresponding to affected proteins; and (7) at least one routine for searching the new image outside of the set of matched new image spots to determine the position and IOD % of unidentified new image spots corresponding to proteins, wherein the spots detected in steps 6 and 7 represent affected proteins.

2. The computer program product of claim 1, wherein said at least one routine for generating a master composite image comprises:

(a) determining a set of selected images, wherein each selected image in the set has a background and corresponding spots that correspond to corresponding spots in the other selected images; and (b) averaging the set of selected images, wherein the averaging comprises
 (i) computing an average composite background from the backgrounds of the set of selected images;
 (ii) averaging the IOD % of corresponding spots in the set of selected images to form an average composite IOD % for each master composite spot;
 (iii) averaging a physical shape of corresponding spots in the set of selected images to form an average physical shape for each master composite spot;
 (iv) averaging the spot position of corresponding spots in the set of selected images to form an average spot position for each master composite spot;
 (v) computing a standard deviation for the average composite IOD % for each master composite spot; and
 (vi) computing a standard deviation for the average spot position for each master composite spot.

3. The computer program product of claim 1, wherein the at least one routine for aligning the new image with the master composite image comprises:

(a) identifying a common anchor point, wherein the common anchor point corresponds to a new image common anchor spot and to a master composite common anchor spot;

(b) determining the position of the master composite common anchor spot;

(c) determining the position of the new image common anchor spot; and (d) applying a position correction so that the position of the new image common anchor spot is aligned with the position of the master composite common anchor spot.

4. The computer program product of claim 3, further comprising:

(e) determining a spot identifier for the master composite common anchor spot; and (f) assigning the new image common anchor spot a spot identifier that is the same as the spot identifier for the master composite common anchor point.

5. The computer program product of claim 1, wherein said at least one routine for aligning the new image with the master composite image comprises:

(a) searching the master composite to identify a predetermined number of primary anchor points, wherein each of the predetermined number of primary anchor points
 (i) is separated from the other of the predetermined number of primary anchor points by at least a predetermined separation threshold, and
 (ii) has a saturation value that falls within a predetermined saturation value range.

6. The computer program product of claim 5, wherein each of said predetermined number of primary anchor points has a standard deviation percentage (SD %) for the average composite IOD % that is less than 40%.

7. The computer program product of claim 5, wherein the step of searching the master composite to identify a predetermined number of primary anchor points comprises:

(a) for each anchor point in the set of anchor points,
 (i) determining an X position coordinate and a Y position coordinate corresponding to the position of the anchor point;
 (ii) determining the IOD % for the anchor point;
 (iii) determining the spot number for the anchor point;
 (iv) searching the new image in a region defined by said X position coordinate ± an X position coordinate tolerance and by the Y position coordinate ± a Y position coordinate tolerance to locate a new image spot that has an IOD % equal to the IOD % for the anchor point±20%;

(v) if a new image spot is located in step (iv), assigning the located new image spot a spot identifier that is the same as the spot identifier for the anchor point.

8. The computer program product of claim 5, wherein said at least one routine for aligning the new image with the master composite image further comprises:

(a) selecting from the master composite all master composite spots that have a saturation value S so that 0.2<S<0.8 to form a first set of selected master composite spots; and (b) selecting from the first set of selected master composite spots a set of secondary anchor points so tat each selected master composite spot in the set of secondary anchor points is separated from the other selected master composite spots in the set of secondary anchor points by at least 3 mm.

9. The computer program product of claim 8, wherein said at least one routine for aligning the new image with the master composite image further comprises:

(a) determining an X position coordinate and a Y position coordinate corresponding to the position of the secondary anchor point;

(b) determining the IOD % for the secondary anchor point;

(c) determining the spot number for the secondary anchor point;

(d) searching the new image in a region defined by the X position coordinate ± an X position coordinate tolerance and by a Y position coordinate ± a Y position coordinate tolerance to locate a new image spot that has an IOD % equal to the IOD % for the anchor point±20%;

(e) if a new image spot is located, assigning the located new image spot a spot identifier that is the same as the spot identifier for the secondary anchor point.

10. The method of claim 1, wherein step (6) comprises:

(a) for each spot in the master composite image
   (i) determining an X position coordinate and a Y position coordinate corresponding to the position of the spot:
   (ii) determining the spot identifier for the spot;
   (iii) searching the new image in a region defined by the X position coordinate ± an X position coordinate tolerance and by the Y position coordinate ± a Y position coordinate tolerance to locate a new image spot in the location defined thereby; and
   (iv) if a new image spot is located, assigning the located new image spot a spot identifier that is the same as the spot identifier for the corresponding master composite spot.

11. The computer program product of claim 10, wherein said X position coordinate tolerance is 0.1 mm and the Y position coordinate tolerance is 0.1 mm.

12. The computer program product of claim 1, further comprising:

(a) at least one routine for enabling the processor to search the new image using a first sensitivity to locate a first set of unidentified new image spots; and (b) at least one routine for enabling the processor to search the new image outside of the set of matched new image spots and the first set of unmatched new image spots using a second sensitivity that is higher than the first sensitivity and a shape criterion to locate a second set of unidentified new image spots.

13. A computer program product according to claim 1, further comprising at least one routine for enabling the processor to compare a first set of images to a second set of images, wherein said comparing means comprises:

(i) at least one routine for enabling the processor to compute a statistical average of IOD % for each spot in the first set;

(ii) at least one routine for enabling the processor to determine if each spot in the first set is statistically different from each spot in the second set; and (iii) at least one routine for enabling the processor to determine if each spot in the first set is statistically different from each spot in the second set.

14. The computer program product of claim 1, wherein the position of the master composite spots and the position of the new image spots are expressed in rectangular parallel coordinates.

* * * * *